(12) United States Patent
Van Hijum et al.

(10) Patent No.: US 6,730,502 B2
(45) Date of Patent: May 4, 2004

(54) FRUCTOSYLTRANSFERASES

(75) Inventors: Sacha Adrianus Fokke Taco Van Hijum, Groningen (NL); Gerritdina Hendrika Van Geel-Schutten, Driebergen-Rijsenberg (NL); Lubbert Dijkhuizen, Zuidlaren (NL); Hakim Rahaoui, Amersfoort (NL)

(73) Assignee: Nederlandse Organisatie voor Toegepast - Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/995,587

(22) Filed: Nov. 29, 2001

(65) Prior Publication Data

US 2002/0127681 A1 Sep. 12, 2002

Related U.S. Application Data

(63) Continuation-in-part of application No. 09/604,958, filed on Jun. 28, 2000, now Pat. No. 6,635,460.

(30) Foreign Application Priority Data

May 25, 2000 (EP) .............................. 00201872

(51) Int. Cl.$^7$ .......................... C12N 9/10; C12P 19/18; C12P 19/04
(52) U.S. Cl. .................... 435/97; 435/101; 435/193; 435/252.9
(58) Field of Search .................. 435/97, 101, 193, 435/252.9

(56) References Cited

PUBLICATIONS

G.H. van Geel–Schutten et al. "Biochemical and Structural Characterization of the Glucan and Fructan Exoplysaccharides Synthesized by the *Lactobacillus reuteri* Wild–Type Strain and by Mutant Strains", Applied Environ. Microbiol. 65(7); 3008–3014. (Jul. 1).*

G.H. van Geel–Schutten et al. "Screening and Charcterization of Lactobacillus Strains Producing Large Amounts of Exopolysaccharides", Appl. Microbiol. Biotechnol. 50: 697–703. (1998).*

* cited by examiner

*Primary Examiner*—Rebecca Prouty
(74) *Attorney, Agent, or Firm*—Young & Thompson

(57) ABSTRACT

The present invention describes two novel proteins having fructosyltransferase activity. Both enzymes are derived from lactobacilli, which are food-grade micro-organisms with the Generally Recognized As Safe (GRAS) status. One of these proteins produces an inulin and fructo-oligosaccharides, while the other produces a levan and fructo-oligosaccharides. According to the invention lactobacilli capable of producing an inulin and/or a levan and/or fructo-oligosaccharides using one or both of the fructosyltransferases can be used as a probiotic or a symbiotic.

8 Claims, 8 Drawing Sheets

Fig 1 ( 1 )

```
  1 tacaatgggg tggcggaggt gaagaaacgg ggttacttct atgctagaac gcaaggaaca 19ftf>
    y  n  g  v  a  e  v  k  k  r  g  y  f  y  a  r  t
    y  n  g  v  a  e  v  n  t  e  r  q  a  n  g  q  1

61 taaaaaaatg tataaaagcg gtaaaaattg ggcagtcgtt acactctcga ctgctgcgct
  1          m  y  k  s  g  k  n  w  a  v  v  t  l  s  t  a  a 121 ggtatttggt gcaacaactg taaatgcatc cgcggacaca aatattgaaa acaatgattc
 18 l  v  f  g  a  t  t  v  n  a  s  a  d  t  n  i  e  n  n  d 181 ttctactgta caagttacaa caggtgataa tgatattgct gttaaaagtg tgacacttgg
 38 s  s  t  v  q  v  t  t  g  d  n  d  i  a  v  k  s  v  t  l 241 tagtggtcaa gttagtgcag ctagtgatac gactattaga acttctgcta atgcaaatag
 58 g  s  g  q  v  s  a  a  s  d  t  t  i  r  t  s  a  n  a  n 301 tgcttcttct gccgctaata cacaaaattc taacagtcaa gtagcaagtt ctgctgcaat
 78 s  a  s  s  a  a  n  t  q  n  s  n  s  q  v  a  s  s  a  a 361 aacatcatct acaagttccg cagcttcatt aaataacaca gatagtaaag cggctcaaga
 98 i  t  s  s  t  s  s  a  a  s  l  n  n  t  d  s  k  a  a  q 421 aaatactaat acagccaaaa atgatgacac gcaaaaagct gcaccagcta acgaatcttc
118 e  n  t  n  t  a  k  n  d  d  t  q  k  a  a  p  a  n  e  s 481 tgaagctaaa aatgaaccag ctgtaaacgt taatgattct tcagctgcaa aaaatgatga
138 s  e  a  k  n  e  p  a  v  n  v  n  d  s  s  a  a  k  n  d 541 tcaacaatcc agtaaaaaga atactaccgc taagttaaac aaggatgctg aaaacgttgt
158 d  q  q  s  s  k  k  n  t  t  a  k  l  n  k  d  a  e  n  v 601 aaaaaaggcg ggaattgatc ctaacagttt aactgatgac cagattaaag cattaaataa
178 v  k  k  a  g  i  d  p  n  s  l  t  d  d  q  i  k  a  l  n
```

Fig 1 ( 2 )

```
 661 gatgaacttc tcgaaagctg caaagtctgg tacacaaatg acttataatg atttccaaaa
 198 k  m  n  f   s  k  a  a  k  s   g  t  q  m   t  y  n   d  f  q 721 gattgctgat acgttaatca aacaagatgg tcggtacaca gttccattct ttaaagcaag  20ftfi <
 218 k  i  a  d  t  l  i  k  q  d  g  r  y  t   v  p  f   f  k  a 781 tgaaatcaaa aatatgcctg ccgctacaac taaagatgca caaactaata ctattgaacc
 238 s  e  i  k  n  m  p   a  a  t   t  k  d  a  q  t  n   t  i  e 841 tttagatgta tgggattcat ggccagttca agatgttcgg acaggacaag ttgctaattg   5ftf >
 258 p  l  d  v   w  d  s   w  p  v   q  d  v  r   t  g  q   v  a  n    8ftfi <

901 gaatggctat caacttgtca tcgcaatgat gggaattcca aaccaaaatg ataatcatat
 278 w  n  g  y   q  l  v   i  a  m   m  g  i  p   n  q  n   d  n  h 961 ctatctctta tataataagt atggtgataa tgaattaagt cattggaaga atgtaggtcc   7ftf >
 298 i  y  l  l   y  n  k   y  g  d   n  e  l  s   h  w  k   n  v  g 1021 aattttttggc tataattcta ccgcggtttc acaagaatgg tcaggatcag ctgttttgaa  7ftf >
 318 p  i  f  g   y  n  s   t  a  v   s  q  e  w   s  g  s   a  v  l    6ftfi <

1081 cagtgataac tctatccaat tattttatac aagggtagac acgtctgata acaataccaa
 338 n  s  d  n   s  i  q   l  f  y   t  r  v  d   t  s  d   n  n  t 1141 tcatcaaaaa attgctagcg ctactcttta tttaactgat aataatggaa atgtatcact  NheI
 358 n  h  q  k   i  a  s   a  t  l   y  l  t  d   n  n  g   n  v  s   AC1(i)<>

1201 cgctcaggta cgaaatgact atattgtatt tgaaggtgat ggctattact accaaactta  AC2(i)<>
 378 l  a  q  v   r  n  d   y  i  v   f  e  g  d   g  y  y   q  t 1261 tgatcaatgg aaagctacta acaaaggtgc cgataatatt gcaatgcgtg atgctcatgt
 398 y  d  q  w   k  a  t   n  k  g   a  d  n  i   a  m  r   d  a  h
```

Fig 1 ( 3 )

```
1321 aattgaagat ggtaatggtg atcggtacct tgttttgaa gcaagtactg gtttggaaaa
 418 v  i  e  d  g  n  g  d  r  y  l  v  f  e  a  s  t  g  l  e 1381 ttatcaaggc gaggaccaaa tttataactg gttaaattat ggcggagatg acgcatttaa
 438 n  y  q  g  e  d  q  i  y  n  w  l  n  y  g  g  d  d  a  f 1441 tatcaagagc ttatttagaa ttctttccaa tgatgatatt aagagtcggg caacttgggc
 458 n  i  k  s  l  f  r  i  l  s  n  d  d  i  k  s  r  a  t  w 1501 taatgcagct atcggtatcc tcaaactaaa taaggacgaa aagaatccta aggtggcaga
 478 a  n  a  a  i  g  i  l  k  l  n  k  d  e  k  n  p  k  v  a 1561 gttatactca ccattaattt ctgcaccaat ggtaagcgat gaaattgagc gaccaaatgt
 498 e  l  y  s  p  l  i  s  a  p  m  v  s  d  e  i  e  r  p  n 1621 agttaaatta ggtaataaat attacttatt tgccgctacc cgtttaaatc gaggaagtaa
 518 v  v  k  l  g  n  k  y  y  l  f  a  a  t  r  l  n  r  g  s 1681 tgatgatgct tggatgaatg ctaattatgc cgttggtgat aatgttgcaa tggtcggata
 538 n  d  d  a  w  m  n  a  n  y  a  v  g  d  n  v  a  m  v  g 1741 tgttgctgat agtctaactg gatcttataa gccattaaat gattctggag tagtcttgac
 558 y  v  a  d  s  l  t  g  s  y  k  p  l  n  d  s  g  v  v  l 1801 tgcttctgtt cctgcaaact ggcggacagc aacttattca tattatgctg tccccgttgc
 578 t  a  s  v  p  a  n  w  r  t  a  t  y  s  y  y  a  v  p  v 1861 cggaaaagat gaccaagtat tagttacttc atatatgact aatagaaatg gagtagcggg
 598 a  g  k  d  d  q  v  l  v  t  s  y  m  t  n  r  n  g  v  a 1921 taaaggaatg gattcaactt gggcaccgag tttcttacta caaattaacc cggataacac 12ftfi <
 618 g  k  g  m  d  s  t  w  a  p  s  f  l  l  q  i  n  p  d  n
```

Fig 1 ( 4 )

```
1981 aactactgtt ttagctaaaa tgactaatca aggggattgg atttgggatg attcaagcga
 638 t   t   v   l   a   k   m   t   n   q   g   d   w   i   w   d   d   s   s 2041 aaatcttgat atgattggtg atttagactc cgctgcttta cctggcgaac gtgataaacc
 658 e   n   l   d   m   i   g   d   l   d   s   a   a   l   p   g   e   r   d   k 2101 tgttgattgg gacttaattg gttatggatt aaaaccgcat gatcctgcta caccaaatga
 678 p   v   d   w   d   l   i   g   y   g   l   k   p   h   d   p   a   t   p   n 2161 tcctgaaacg ccaactacac cagaaacccc tgagacacct aatactccca aaacaccaaa
 698 d   p   e   t   p   t   t   p   e   t   p   e   t   p   n   t   p   k   t   p 2221 gactcctgaa aatcctggga cacctcaaac tcctaataca cctaatactc cggaaattcc
 718 k   t   p   e   n   p   g   t   p   q   t   p   n   t   p   n   t   p   e   i 2281 tttaactcca gaaacgccta agcaacctga aacccaaact aataatcgtt tgccacaaac
 738 p   l   t   p   e   t   p   k   q   p   e   t   q   t   n   n   r   l   p   q 2341 tggaaataat gccaataaag ccatgattgg cctaggtatg ggaacattgc ttagtatgtt
 758 t   g   n   n   a   n   k   a   m   i   g   l   g   m   g   t   l   l   s   m 2401 tggtcttgca gaaattaaca aacgtcgatt taactaaata ctttaaaata aaaccgctaa
 778 f   g   l   a   e   i   n   k   r   r   f   n 2461 gccttaaatt cagcttaacg gttttttatt ttaaagttt  ttattgtaaa aaagcgaatt 2521 atcattaata ctaatgcaat tgttgtaaga ccttacgaca gtagtaacaa tgaatttgcc 2581 catctttgtc gg
```

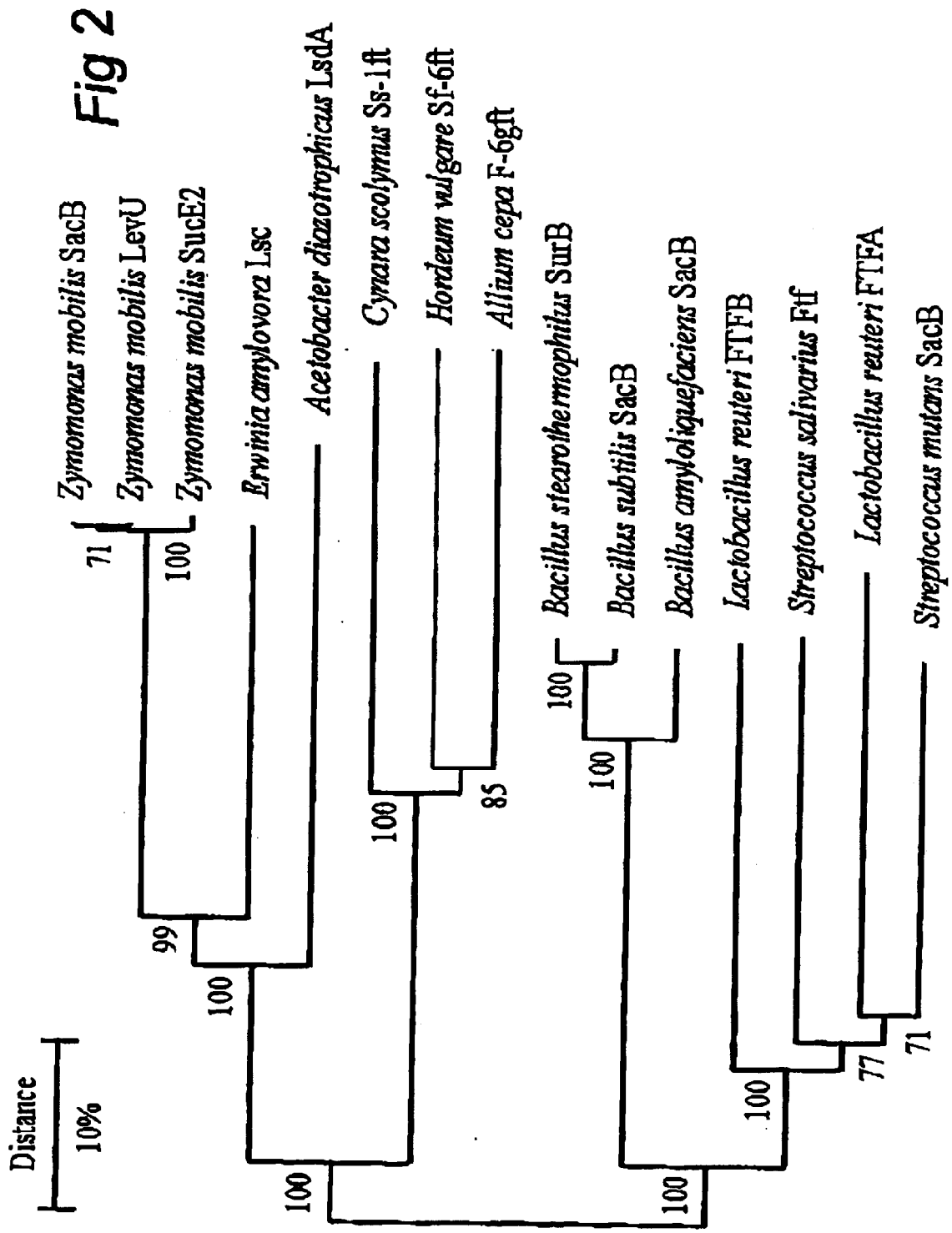

Fig 3

The N-terminal sequence of FTFB (levansucrase):
(A) Q V E S N N Y N G V A E V N T E R Q A N G Q I (G) (V) (D).

Internal peptide sequences of FTFB (levansucrase):
- (M) (A) H L D V W D S W P V Q D P (V),
- N A G S I F G T (K),
- V (E) (E) V Y S P K V S T L M A S D E V E.

Fig 4

5ftf
| | | | |
|---|---|---|---|
| B. amyloliquefaciens SacB | 80 | GLDVMDSWPLQNAD | 93 |
| B. subtilis SacB | 82 | GLDVMDSWPLQNAD | 95 |
| S. mutans SacB | 243 | DLDVMDSWPVQDAK | 256 |
| S. salivarius Ftf | 282 | EIDVMDSWPVQDAK | 295 |
| | | :******.:*.:*. | |

6ftf
| | | | |
|---|---|---|---|
| B. amyloliquefaciens SacB | 156 | QTQENSGSATFTSDGK | 171 |
| B. subtilis SacB | 158 | QTQEWSGSATFTSDGK | 173 |
| S. mutans SacB | 312 | LTQEWSGSATVNEDGS | 327 |
| S. salivarius Ftf | 351 | DDQQWSGSATVNSDGS | 366 |
| | | *:****.... | |

12ftf
| | | | |
|---|---|---|---|
| B. amyloliquefaciens SacB | 440 | KATFGPSFLMN | 450 |
| B. subtilis SacB | 440 | QSTFAPSFLLN | 450 |
| S. mutans SacB | 609 | NSTWAPSFLIQ | 619 |
| S. salivarius Ftf | 655 | KSTWAPSFLIK | 665 |
| | | ::*:.****:: | |

FRUCTOSYLTRANSFERASES

CROSS-REFERENCE TO RELATED APPLICATION

This application is a continuation-in-part of application of U.S. application Ser. No. 09/604,958 filed on Jun. 28, 2000, now U.S. Pat. No. 6,635,460, which claims priority from European Application No. 00201872.9 filed on May 25, 2000.

The present invention is in the field of enzymatic production of biomolecules. The invention is particularly concerned with two novel fructosyltransferases derived from lactobacilli and with a process for recombinant production of the enzymes and for the production of useful levans, inulins and fructo-oligosaccharides from sucrose.

BACKGROUND OF THE INVENTION

Lactic acid bacteria (LAB) play an important role in the fermentative production of food and feed. Traditionally, these bacteria have been used for the production of for instance wine, beer, bread, cheese and yoghurt, and for the preservation of food and feed, e.g. olives, pickles, sausages, sauerkraut and silage. Because of these traditional applications, lactic acid bacteria are food-grade microorganisms that posses the Generally Recognised As Safe (GRAS) status. Due to the different products which are formed during fermentation with lactic acid bacteria, these bacteria contribute positively to the taste, smell and preservation of the final product. The group of lactic acid bacteria encloses several genera such as Lactobacillus, Leuconostoc, Pediococcus, Streptococcus, etc.

In recent years also the health promoting properties of lactic acid bacteria have received much attention. They produce an abundant variety of exopolysaccharides (EPS's). These polysaccharides are thought to contribute to human health by acting as prebiotic substrates, nutraceuticals, cholesterol lowering agents or immunomodulants.

To date high molecular weight polysaccharides produced by plants (such as cellulose, starch and pectin), seaweeds (such as alginate and carrageenan) and bacteria (such as alginate, gellan and xanthan) are used in several industrial applications as viscosifying, stabilising, emulsifying, gelling or water binding agents. Although all these polysaccharides are used as food additives, they originate from organisms not having the GRAS status. Thus they are less desirable than the exopolysaccharides of microorganisms, such as lactic acid bacteria, which have the GRAS status.

The exopolysaccharides produced by LAB can be divided in two groups, heteropolysaccharides and homopolysaccharides; these are synthesized by totally different mechanisms. The former consist of repeating units in which residues of different types of sugars are present and the latter consist of one type of monosaccharide. The synthesis of heteropolysaccharides by lactic acid bacteria, including lactobacilli, has been studied extensively in recent years. Considerably less information is available on the synthesis of homopolysaccharides from lactobacilli, although some studies have been performed. Homopolysaccharides with fructose as the constituent sugar can be divided into two groups, inulins and levans. Inulins consist of 2,1-linked β-fructofuranoside residues, whereas levans consist of 2,6-linked β-fructofuranoside residues. Both can be linear or branched. The size of bacterial levans can vary from 20 kDa up to several MDa. There is limited information on the synthesis of levans. In most detail this synthesis has been studied in *Zymomonas mobilis* and in Bacillus species. Within lactic acid bacteria, fructosyltransferases have only been studied in streptococci. So far no fructosyltransferases have been reported in lactobacilli.

In a recent report the *Lactobacillus reuteri* strain LB 121 was found to produce both a glucan and a fructan when grown on sucrose, but only a fructan when grown on raffinose (van Geel-Schutten, G. H. et al., Appl. Microbiol. Biotechnol. (1998) 50, 697–703). In another report the glucan and fructan were characterised by their molecular weights (of 3,500 and 150 kDa respectively) and the glucan was reported to be highly branched with a unique structure consisting of a terminal, 4-substituted, 6-substituted, and 4,6-disubstituted α-glucose in a molar ratio 1.1: 2.7:1.5:1.0 (van Geel-Schutten, G. H. et al., Appl. Environ. Microbiol. (1999) 65, 3008–3014). The fructan was identified as a linear (2→6)-β-D-fructofuranan (also called a levan). This was the first example of fructan synthesis by a Lactobacillus species.

SUMMARY OF THE INVENTION

Two novel genes encoding enzymes having fructosyltransferase activity have now been found in *Lactobacillus reuteri*, and their amino acid sequences have been determined. These are the first two enzymes identified in a Lactobacillus species capable of producing a fructan. One of the enzymes is an inulosucrase which produces a high molecular weight ($>10^7$ Da) fructan containing β(2-1) linked fructosyl units and fructo-oligosaccharides, while the other is a levansucrase which produces a fructan containing β(2-6) linked fructosyl units. The invention thus pertains to the enzymes, to DNA encoding them, to recombinant cells containing such DNA and to their use in producing carbohydrates, as defined in the appending claims.

DESCRIPTION OF THE INVENTION

It was found according to the invention that one of the novel fructosyltransferases (FTFA; an inulosucrase) produces a high molecular weight inulin with β(2-1) linked fructosyl units and fructo-oligosaccharides. The fructo-oligosaccharides synthesis was also observed in certain Lactobacillus strains, in particular in certain strains of *Lactobacillus reuteri*. However, the inulin has not been found in *Lactobacillus reuteri* culture supernatants, but only in extracts of *E. coli* cells expressing the above-mentioned fructosyltransferase. This inulosucrase consists of either 798 amino acids (2394 nucleotides) or 789 amino acids (2367 nucleotides) depending on the potential start codon used. The molecular weight (MW) deduced of the amino acid sequence of the latter form is 86 kDa and its isoelectric point is 4.51, at pH 7.

The amino acid sequence of the inulosucrase is shown in SEQ ID No. 1 (FIG. 1, amino acid residues 1–789). As mentioned above, the nucleotide sequence contains two putative start codons leading to either a 2394 (see SEQ ID No. 3) or 2367 (see SEQ ID No. 2) nucleotide form of the inulinsucrase. Both putative start codons are preceded by a putative ribosome binding site, GGGG (located 12 base pairs upstream its start codon) or AGGA (located 14 base pairs upstream its start codon), respectively (see FIG. 1 and SEQ ID No. 4).

The present invention covers a protein having inulosucrase activity with an amino acid identity of at least 65%, preferably at least 75%, and more preferably at least 85%, compared to the amino acid sequence of SEQ ID No. 1. The invention also covers a part of a protein with at least 15 contiguous amino acids which are identical to the corresponding part of the amino acid sequence of SEQ ID No. 1.

Fructosyltransferases have been found in several bacteria such as *Zymomonas mobilis, Erwinia amylovora, Acetobacter amylovora, Bacillus polymyxa, Bacillus amyloliquefaciens, Bacillus stearothermophilus,* and *Bacillus subtilis.* In lactic acid bacteria this type of enzyme previously has only been found in some streptococci. Most bacterial fructosyltransferases have a molecular mass of 50–100 kDa (with the exception of the fructosyltransferase found in *Streptococcus salivarius* which has a molecular mass of 140 kDa). Amino acid sequence alignment revealed that the novel inulosucrase of lactobacilli has high homology with fructosyltransferases originating from Gram positive bacteria, in particular with Streptococcus enzymes. The highest homology (FIG. 2) was found with the SacB enzyme of *Streptococcus mutans* Ingbritt A (62% identity within 539 amino acids).

Certain putative functions based on the alignment and site-directed mutagenesis studies can be ascribed to several amino acids of the novel inulosucrase. Asp-263, Glu-330, Asp-415, Glu-431, Asp-511, Glu-514, Arg-532 and/or Asp-551 of the amino acid sequence of SEQ ID No. 1 are identified as putative catalytic residues. Noteworthy, a hydrophobicity plot according to Kyte and Doolittle (1982) J. Mol. Biol. 157, 105–132 suggests that the novel inulosucrase contains a putative signal sequence according to the Von Heijne rule. The putative signal peptidase site is located between Gly at position 21 and Ala at position 22. Furthermore, it is striking that the C-terminal amino acid sequence of the novel inulosucrase contains a putative cell wall anchor amino acid signal LPXTG (SEQ ID No. 5) and a 20-fold repeat of the motif PXX (residues 690–749 of SEQ ID NO: 1) (see figure 1.), where P is proline and X is any other amino acid. In 15 out of 20 repeats, however, the motif is PXT. This motif has so far not been reported in proteins of prokaryotic and eukaryotic origin.

A nucleotide sequence encoding any of the above mentioned proteins, mutants, variants or parts thereof is also a subject of the invention. Furthermore, the nucleic acid sequences corresponding to expression-regulating regions (promoters, enhancers, terminators) of at least 30 contiguous nucleic acids contained in the nucleic acid sequence (-67)-(-1) or 2367–2525 of SEQ ID No. 4 (see also FIG. 1) can be used for homologous or heterologous expression of genes. Such expression-regulating sequences are operationally linked to a polypeptide-encoding nucleic acid sequence such as the genes of the fructosyltransferase according to the invention. A nucleic acid construct comprising the nucleotide sequence operationally linked to an expression-regulating nucleic acid sequence is also covered by the invention.

A recombinant host cell, such as a mammalian (with the exception of human), plant, animal, fungal or bacterial cell, containing one or more copies of the nucleic acid construct mentioned above is an additional subject of the invention. The inulosucrase gene (starting at nucleotide 41) has been cloned in an *E. coli* expression vector under the control of an ara promoter in *E. coli* Top10. *E. coli* Top10 cells expressing the recombinant inulosucrase hydrolysed sucrose and synthesized fructan material. SDS-PAGE of arabinose induced *E. coli* Top10 cell extracts suggested that the recombinant inulosucrase has a molecular weight of 80–100 kDa, which is in the range of other known fructosyltransferases and in line with the molecular weight of 86 kDa deduced of the amino acid sequence depicted in FIG. 1.

The invention further covers an inulosucrase according to the invention which, in the presence of sucrose, produces a inulin having β(2-1)-linked D-fructosyl units and fructo-oligosaccharides. Two different types of fructans, inulins and levans, exist in nature. Surprisingly, the novel inulosucrase expressed in *E. coli* Top10 cell synthesizes a high molecular weight (>$10^7$ Da) inulin and fructo-oligosaccharides, while in *Lactobacillus reuteri* culture supernatants, in addition to the fructo-oligosaccharides, a levan and not an inulin is found. This discrepancy can have several explanations: the inulosucrase gene may be silent in *Lactobacillus reuteri*, or may not be expressed in *Lactobacillus reuteri* under the conditions tested, or the inulosucrase may only synthesize fructo-oligosaccharides in its natural host, or the inulin polymer may be degraded shortly after synthesis, or may not be secreted and remains cell-associated, or the inulosucrase may have different activities in *Lactobacillus reuteri* and *E. coli* Top10 cells.

It was furthermore found according to the invention that certain lactobacilli, in particular *Lactobacillus reuteri*, possess another fructosyltransferase, a levansucrase (FTFB), in addition to the inulosucrase described above. The N-terminal amino acid sequence of the fructosyltransferase purified from Lactobacillus reuteri supernatant was found to be QVESNNYNGVAEVNTERQANGQI (residues 2–24 of SEQ ID No. 6). Furthermore, three internal sequences were identified, namely (M)(A)HLDVWDSWPVQDP(V) (SEQ ID No. 7), NAGSIFGT(K) (SEQ ID No. 8), V(E) (E) VYSPKVSTLMASDEVE (SEQ ID No. 9). The N-terminal amino acid sequence could not be identified in the deduced inulosucrase sequence. Also the amino acid sequences of the three internal peptide fragments of the purified fructosyltransferase were not present in the putative inulosucrase sequence. Evidently, the inulosucrase gene does not encode the purified fructosyltransferase synthesizing the levan. The complete amino acid sequence of the levansucrase is shown in SEQ ID No. 11 and the nucleotide sequence is shown in SEQ ID No. 10. The levansucrase comprises a putative membrane anchor (see amino acids 761–765 in SEQ ID No. 11) and a putative membrane spanning domain (see amino acids 766–787 in SEQ ID No. 11). The fructan produced by the levansucrase was identified in the Lactobacillus reuteri culture supernatant as a linear (2→6)-β-D-fructofuranan with a molecular weight of 150 kDa. The purified enzyme also produces this fructan.

Additionally, the invention thus covers a protein having levansucrase activity with an amino acid identity of at least 65%, preferably at least 75%, and more preferably at least 85%, compared to the amino acid sequence of SEQ ID NO. 11. The second novel fructosyltransferase produces a high molecular weight fructan with β(2-6) linked fructosyl units with sucrose or raffinose as substrate. The invention also covers a part of a protein with least 15 contiguous amino acids, which are identical to the corresponding part of the amino acid sequence of SEQ ID No. 11. A nucleotide sequence encoding any of the above-mentioned proteins, mutants, variants or parts thereof is a subject of the invention as well as a nucleic acid construct comprising the nucleotide sequence mentioned above operationally linked to an expression-regulating nucleic acid sequence. A recombinant host cell, such as a mammalian (with the exception of human), plant, animal, fungal or bacterial cell, containing one or more copies of the nucleic acid construct mentioned above is an additional subject of the invention. The invention further covers a protein according to the invention which, in the presence of sucrose, produces a fructan having β(2-6)-linked D-fructosyl units.

The invention also pertains to a process of producing an inulin-type and/or a levan-type of fructan as described above using fructosyltransferases according to the invention and a suitable fructose source such as sucrose, stachyose or raffinose. The fructans may either be produced by Lactobacillus strains or recombinant host cells according to the invention containing one or both fructosyl transferases or by a fuctosyltransferase enzyme isolated by conventional means from the culture of fructosyltransferase-positive lactobacilli, especially a *Lactobacillus reuteri*, or from a recombinant organism containing the fructosyltransferase gene or genes.

Additionally, the invention concerns a process of producing fructo-oligosaccharides containing the characteristic structure of the fructans described above using a Lactobacillus strain or a recombinant host cell according to the invention containing one or both fructosyltransferases or an isolated fructosyltransferase according to the invention. There is a growing interest in oligosaccharides derived from homopolysaccharides, for instance for prebiotic purposes. Several fructo- and gluco-oligosaccharides are known to stimulate the growth of bifidobacteria in the human colon. Fructo-oligosaccharides produced by the fructosyltransferase described above are also part of the invention. Another way of producing fructo-oligosaccharides is by hydrolysis of the fructans described above. This hydrolysis can be performed by known hydrolysis methods such as enzymatic hydrolysis with enzymes such as levanase or inulinase or by acid hydrolysis. The fructo-oligosaccharides can also be produced in the presence of a fructosyltransferase according to the invention and an acceptor molecule such as lactose or maltose. The fructo-oligosaccharides to be produced according to the invention prefarably contain at least 2, more preferably at least 3, up to about 20 anhydrofructose units, optionally in addition to one or more other (glucose, galactose, etc.) units. These fructo-oligosaccharides are useful as prebiotics, and can be administered to a mammal in need of improving the bacterial status of the colon.

The invention also concerns chemically modified fructans and fructo-oligosaccharides based on the fructans described above. Chemical modification can be achieved by oxidation, such as hypochlorite oxidation resulting in ring-opened 2,3-dicarboxy-anhydrofructose units (see e.g. EP-A-427349), periodate oxidation resulting in ring-opened 3,4-dialdehyde-anhydrofructose units (see e.g. WO 95/12619), which can be further oxidised to (partly) carboxylated units (see e.g. WO 00/26257), TEMPO-mediated oxidation resulting in 1- or 6-carboxy-anhydrofructose units (see e.g. WO 95/07303). The oxidised fructans have improved water-solubility, altered viscosity and a retarded fermentability and can be used as metal-complexing agents, detergent additives, strengthening additives, bioactive carbohydrates, emulsifiers and water binding agents. They can also be used as starting materials for further derivatisation such as cross-linking and the introduction of hydrophobes. Oxidised fructans coupled to amino compounds such as proteins, or fatty acids can be used as emulsifiers and stabilizers. (Partial) hydrolysis of fructans according to the invention and modified fructans according to the invention results in fructo-oligosaccharides, which can be used as bioactive carbohydrates or prebiotics. The oxidised fructans of the invention preferably contain 0.05–1.0 carboxyl groups per anhydrofructose unit, e.g. as 6- or 1-carboxyl units.

Another type of chemical modification is phosphorylation, as described in O.B. Wurzburg (1986) Modified Starches: properties and uses. CRC Press Inc., Boca Raton, 97–112. One way to achieve this modification is by dry heating fructans with a mixture of monosodium and disodium hydrogen phosphate or with tripolyphosphate. The phosphorylated fructans are suitable as wet-end additives in papermaking, as binders in paper coating compositions, as warp sizing-agents, and as core binders for sand molds for metal casting. A further type of derivatisation of the fructans is acylation, especially acetylation using acetic or propionic anhydride, resulting in products suitable as bleaching assistants and for the use in foils. Acylation with e.g. alkenyl succinic anhydrides or (activated) fatty acids results in surface-active products suitable as e.g. surfactants, emulsifiers, and stabilizers.

Hydroxyalkylation, carboxymethylation, and aminoalkylation are other methods of chemical derivatisation of the fructans. Hydroxyalkylation is commonly performed by base-catalysed reaction with alkylene oxides, such as ethylene oxide, propylene oxide or epichlorohydrine; the hydroxyalkylated products have improved solubility and viscosity characteristics. Carboxymethylation is achieved by reaction of the fructans with mono-chloroacetic acid or its alkali metal salts and results in anionic polymers suitable for various purposes including crystallisation inhibitors, and metal complexants. Amino-alkylation can be achieved by reaction of the fructans with alkylene imines, haloalkyl amines or amino-alkylene oxides, or by reaction of epichlorohydrine adducts of the fructans with suitable amines. These products can be used as cationic polymers in a variety of applications, especially as a wet-end additive in paper making to increase strength, for filler and fines retention, and to improve the drainage rate of paper pulp. Other potential applications include textile sizing and wastewater purification. The above mentioned modifications can be used either separately or in combination depending on the desired product. Furthermore, the degree of chemical modification is variable and depends on the intended use. If necessary 100% modification, i.e. modification of all anhydrofructose units can be performed. However, partial modification, e.g. from 1 modified anhydrofructose unit per 100 up to higher levels, will often be sufficient in order to obtain the desired effect. The modified fructans have a DP (degree of polymerisation) of at least 100, preferably at least 1000 units.

Use of a Lactobacillus strain capable of producing a levan, inulin or fructo-oligosaccharides or a mixture thereof, as a probiotic, is also covered by the invention. Preferably, the Lactobacillus strain is also capable of producing a glucan, especially an 1,4/1,6-α-glucan as referred to above. The efficacy of some *Lactobacillus reuteri* strains as a probiotics has been demonstrated in various animals such as for instance poultry and humans. The administration of some *Lactobacillus reuteri* strains to pigs resulted in significantly lower serum total and LDL-cholesterol levels, while in children *Lactobacillus reuteri* is used as a therapeutic agent against acute diarrhea. For this and other reasons *Lactobacillus reuteri* strains, which were not reported to produce the glucans or fructans described herein, have been supplemented to commercially available probiotic products. The mode of action of *Lactobacillus reuteri* as a probiotic is still unclear. Preliminary studies indicated that gut colonization by *Lactobacillus reuteri* may be of importance. According to the invention, it was found that the mode of action of *Lactobacillus reuteri* as a probiotic may reside partly in the ability to produce polysaccharides. Lactobacillus strains, preferably *Lactobacillus reuteri* strains, and more preferably *Lactobacillus reuteri* strain LB 121 and other strains containing one or more fructosyltransferase genes encoding proteins capable of producing inulins, levans and/or fructo-oligosaccharides can thus advantageously be used as a probiotic. They can also, together with these polysaccharides, be used as a symbiotic (instead of the term symbiotic, the term synbiotic can also be used). In that respect another part of the invention concerns a probiotic or symbiotic composition containing a Lactobacillus strain capable of producing an inulin, a levan or fructo-oligosaccharides and/or a glucan or a mixture thereof, said production being performed according to the process according to the invention. The probiotic or symbiotic compositions of the invention may be directly ingested with or without a suitable vehicle or used as an additive in conjunction with foods. They can be incorporated into a variety of foods and beverages including, but not limited to, yoghurts, ice creams, cheeses, baked products such as bread, biscuits and cakes, dairy and dairy substitute foods, confectionery products, edible oil compositions, spreads, breakfast cereals, juices and the like.

Furthermore, the invention pertains to a process of improving the microbial status in the mammalian colon comprising administering an effective amount of a Lactobacillus strain capable of producing an oligosaccharide or polysaccharide according ot the invention and to a process of improving the microbial status of the mammalian colon comprising administering an effective amount of an oligosaccharide or polysaccharide produced according to the process according ot the invention.

EXAMPLES

EXAMPLE 1

Isolation of DNA from *Lactobacillus reuteri* Nucleotide Sequence Analysis of the Inulosucrase (ftfA) Gene, Construction of Plasmids for Expression of the Inulosucrase Gene in *E. coli* Top10 Expression of the Inulosucrase gene in *E. coli* Top10 and Identification of the Produced Polysaccharides Produced by the Recombinant Enzyme.

General procedures for cloning, DNA manipulations and agarose gel electrophoresis were essentially as described by Sambrook et al. (1989) Molecular cloning: a laboratory manual, 2nd ed. Cold Spring Harbour Laboratory Press, Cold Spring Harbour, N.Y. Restriction endonuclease digestions and ligations with T4 DNA ligase were performed as recommended by the suppliers. DNA was amplified by PCR techniques using ampliTAQ DNA polymerase (Perkin Elmer) or Pwo DNA polymerase. DNA fragments were isolated from agarose gels using the Qiagen extraction kit (Qiagen GMBH), following the instructions of the suppliers. *Lactobacillus reuteri* strain 121 (LMG 18388) was grown at 37° C. in MRS medium (DIFCO) or in MRS-s medium (MRS medium containing 100 g/l sucrose instead of 20 g/l glucose). When fructo-oligosaccharides production was investigated phosphate was omitted and ammonium citrate was replaced by ammonium nitrate in the MRS-s medium. *E. coli* strains were grown aerobically at 37° C. in LB medium, where appropriate supplemented with 50 μg/ml ampicillin (for selection of recombinant plasmids) or with 0.02% (w/v) arabinose (for induction of the inulosucrase gene).

Total DNA of *Lactobacillus reuteri* was isolated according to Verhasselt et al. (1989) FEMS Microbiol. Lett. 59, 135–140 as modified by Nagy et al. (1995) J. Bacteriol. 177, 676–687.

The inulosucrase gene was identified by amplification of chromosomal DNA of *Lactobacillus reuteri* with PCR using degenerated primers (5 ftf, 6 ftfi, and 12 ftfi, see table 1) based on conserved amino acid sequences deduced from different bacterial fructosyltranferase genes (SacB of *Bacillus amyloliquefaciens*, SacB of *Bacillus subtilis*, *Streptococcus mutans* fructosyltransferase and *Streptococcus salivarius* fructosyltransferase, see FIG. 4) and *Lactobacillus reuteri* DNA as template. Using primers 5 ftf and 6 ftfi, an amplification product with the predicted size of about 234 bp was obtained (FIG. 5A). This 234 bp fragment was cloned in *E. coli* JM109 using the pCR2.1 vector and sequenced. Transformations were performed by electroporation using the BioRad gene pulser apparatus at 2.5 kV, 25 μF and 200 Ω, following the instructions of the manufacturer. Sequencing was performed according to the method of Sanger et al. (1977) Proc. Natl. Acad. Sci. USA 74, 5463–5467. Analysis of the obtained sequence data confirmed that part of a fructosyltransferase (ftf gene had been isolated. The 234 bp amplified fragment was used to design primers 7 ftf and 8 ftfi (see table 1). PCR with the primers 7 ftf and 12 ftfi gave a product of the predicted size of 948 bp (see FIG. 5B); its sequence showed clear similarity with previously characterized fructosyltransferase genes. The 948 bp amplified fragment was used to design the primers ftfAC1(i) and ftfAC2(i) (see table 1) for inverse PCR. Using inverse PCR techniques a 1438 bp fragment of the inulosucrase gene was generated, including the 3' end of the inulosucrase gene (see FIG. 5C). The remaining 5' fragment of the inulosucrase gene was isloated with a combination of standard and inverse PCR techniques. Briefly, *Lactobacillus reuteri* DNA was cut with restriction enzyme XhoI and ligated. PCR with the primers 7 ftf and 8 ftfi, using the ligation product as a template, yielded a 290 bp PCR product which was cloned into pCR2.1 and sequenced. This revealed that primer 8 ftfi had annealed aspecifically as well as specifically yielding the 290 bp product (see FIG. 5D).

At this time, the N-terminal amino acid sequence of a fructosyltransferase enzyme (FTFB) purified from the Lactobacillus reuteri strain 121 was obtained. This sequence consisted of the following 23 amino acids: QVESNNYN-GVAEVNTERQANGQI (residues 2–24 of SEQ ID No. 6). The degenerated primer 19 ftf (YNGVAEV) (residues 8–14 of SEQ ID NO: 6) was designed on the basis of a part of this N-terminal peptide sequence and primer 20 ftfi was designed on the 290 bp PCR product. PCR with primers 19 ftf and 20 ftfi gave a 754 bp PCR product (see FIG. 5E), which was cloned into pCR2.1 and sequenced. Both DNA strands of the entire fructosyltransferase gene were double sequenced. In this way the sequence of a 2.6 kb region of the *Lactobacillus reuteri* DNA, containing the inulosucrase gene and its surroundings were obtained.

The plasmids for expression of the inulosucrase gene in *E. coli* Top10 were constructed as described hereafter. A 2414 bp fragment, containing the inulosucrase gene starting at the first putative start codon at position 41, was generated by PCR, using primers ftfA1 and ftfA2i. Both primers contained suitable restriction enzyme recognition sites (a NcoI site at the 5'end of ftfA1 and a BglII site at the 3'end of ftfA2i). PCR with *Lactobacillus reuteri* DNA, Pwo DNA polymerase and primers ftfA1 and ftfA2i yielded the complete inulosucrase gene flanked by NcoI and BglII restriction sites. The PCR product with blunt ends was ligated directly into pCRbluntII-Topo. Using the NcoI and BglII restriction sites, the putative ftfA gene was cloned into the expression vector pBAD, downstream of the inducible arabinose promoter and in frame upstream of the Myc epitope and the His tag. The pBAD vector containing the inulosucrase gene (pSVH101) was transformed to *E. coli* Top10 and used to study inulosucrase expression. Correct construction of plasmid containing the complete inulosucrase gene was confirmed by restriction enzyme digestion analysis and by sequence analysis, showing an in frame cloning of the inulosucrase gene using the ribosomal binding site provided by the pBAD vector and the first putative start codon (at position 41) of inulosucrase (see FIG. 1).

Plasmid DNA of *E. coli* was isolated using the alkaline lysis method of Birnboim and Doly (1979) Nucleic Acids Res. 7, 1513–1523 or with a Qiagen plasmid kit following the instructions of the supplier. Cells of *E. coli* Top10 with pSVH101 were grown overnight in LB medium containing 0.02% (w/v) arabinose and were harvested by centrifugation. The pellet was washed with 25 mM sodium acetate buffer pH 5.4 and the suspension was centrifuged again. Pelleted cells were resuspended in 25 mM sodium acetate buffer pH 5.4. Cells were broken by sonication. Cell debris and intact cells were removed by centrifugation for 30 min at 4° C. at 10,000×g and the resulting cell free extract was used in the enzyme assays.

The fructosyltranferase activities were determined at 37° C. in reaction buffer (25 mM sodium acetate, pH 5.4, 1 mM $CaCl_2$, 100 g/l sucrose) by monitoring the release of glucose from sucrose, by detecting fructo-oligosaccharides or by determining the amount of fructan polymer produced using *E. coli* cell free extracts or *Lactobacillus reuteri* culture supernatant as enzyme source. Sucrose, glucose and fructose were determined enzymatically using commercially available kits.

Fructan production by *Lactobacillus reuteri* was studied with cells grown in MRS-s medium. Product formation was also studied with cell-free extracts of *E. coli* containing the novel inulosucrase incubated in reaction buffer (1 mg protein/10 ml buffer, incubated overnight at 37° C.). Fructans were collected by precipitation with ethanol. $^1$H-NMR spectroscopy and methylation analysis were performed as described by van Geel-Schutten et al. (1999) Appl. Environ. Microbiol. 65, 3008–3014. The molecular weights of the fructans were determined by high performance size exclusion chromatography coupled on-line with a multi angle laser light scattering and a differential refractive index detector. Fructo-oligosaccharide synthesis was studied in *Lactobacillus reuteri* culture supernatants and in extracts of *E. coli* cells containing the novel inulosucrase incubated in reaction buffer (1 mg protein/10 ml buffer, incubated overnight at 37° C.). Glucose and fructose were determined enzymatically as described above and fructo-oligosaccharides produced were analyzed using a Dionex column. The incubation mixtures were centrifuged for 30 min at 10,000×g and diluted 1:5 in a 100% DMSO solution prior to injection on a Dionex column. A digest of inulin (DP1–20) was used as a standard. Separation of compounds was achieved with anion-exchange chromatography on a CarboPac Pa1 column (Dionex) coupled to a CarboPac PA1 guard column (Dionex). Using a Dionex GP50 pump the following gradient was generated: % eluent B is 5% (0 min); 35% (10 min); 45% (20 min); 65% (50 min); 100% (54–60 min); 5% (61–65 min). Eluent A was 0.1 M NaOH and eluent B was 0.6 M NaAc in a 0.1 M NaOH solution. Compounds were detected using a Dionex ED40 electrochemical detector with an AU working electrode and a Ag/AgCl reference-electrode with a sensitivity of 300 nC. The pulse program used was: +0.1 Volt (0–0.4 s); +0.7 Volt (0.41–0.60 s); −0.1 Volt (0.61–1.00 s). Data were integrated using a Perkin Elmer Turbochrom data integration system. A different separation of compounds was done on a cation exchange column in the calcium form (Benson BCX4). As mobile phase Ca-EDTA in water (100 ppm) was used. The elution speed was 0.4 ml/min at a column temperature of 85° C. Detection of compounds was done by a refractive index (Jasco 830-RI) at 40° C. Quantification of compounds was achieved by using the software program Turbochrom (Perkin Elmer).

SDS-PAGE was performed according to Laemmli (1970) Nature 227, 680–685 using 7.5% polyacrylamide gels. After electrophoresis gels were stained with Coomassie Briljant Blue or an activity staining (Periodic Acid Schiff, PAS) was carried out as described by Van Geel-Schutten et al. (1999) Appl. Environ. Microbiol. 65, 3008–3014.

TABLE 1

Nucleotide sequence of primers used in PCR reactions to identify the inulosucrase gene.

| Primer name | Location (bp) | Nucleotide sequence (and SEQ ID No) |
|---|---|---|
| ftfAC1 | 1176 | CTG-ATA-ATA-ATG-GAA-ATG-TAT-CAC (SEQ ID No. 12) |
| ftfAC2i | 1243 | CAT-GAT-CAT-AAG-TTT-GGT-AGT-AAT-AG (SEQ ID No. 13) |
| ftfac1 | 1176 | GTG-ATA-CAT-TTC-CAT-TAT-TAT-CAG (SEQ ID No. 14) |
| ftfAC2 | 1243 | CTA-TTA-CTA-CCA-AAC-TTA-TGA-TCA-TG (SEQ ID No. 15) |
| ftfA1 | | CCA-TGG-CCA-TGG-TAG-AAC-GCA-AGG-AAC-ATA-AAA-AAA-TG (SEQ ID No. 16) |
| ftfA2i | | AGA-TCT-AGA-TCT-GTT-AAA-TCG-ACG-TTT-GTT-AAT-TTC-TG (SEQ ID No. 17) |
| 5ftf | 845 | GAY-GTN-TGG-GAY-WSN-TGG-GCC (SEQ ID No. 18) |
| 6ftfi | 1052 | GTN-GCN-SWN-CCN-SWC-CAY-TSY-TG (SEQ ID No. 19) |
| 7ftf | 1009 | GAA-TGT-AGG-TCC-AAT-TTT-TGG-C (SEQ ID No. 20) |
| 8ftfi | 864 | CCT-GTC-CGA-ACA-TCT-TGA-ACT-G (SEQ ID No. 21) |
| 12ftfi | 1934 | ARR-AAN-SWN-GGN-GCV-MAN-GTN-SW (SEQ ID No. 22) |
| 19ftf | 1 | TAY-AAY-GGN-GTN-GCN-GAR-GTN-AA (SEQ ID No. 23) |
| 20ftfi | 733 | CCG-ACC-ATC-TTG-TTT-GAT-TAA-C (SEQ ID No. 24) |

Listed from left to right are: primer name (i, inverse primer), location (in bp) in ftfA and the sequence from 5' to 3' according to IUB group codes (N = any base; M = A or C; R = A or G; W = A or T; S = C or G; Y = C or T; K = G or T; B = not A; D = not C; H = not G; and V = not T).

EXAMPLE 2

Purification and Amino Acid Sequencing of the Levansucrase (FTFB).

Protein Purification

Samples were taken between each step of the purification process to determine the enzyme activity (by glucose GOD-Perid method) and protein content (by Bradford analysis and acrylamide gel electrophoresis). Collected chromatography fractions were screened for glucose liberating activity (GOD-Perid method) to determine the enzyme activity.

One liter of an overnight culture of LB121 cells grown on MRS medium containing 50 grams per liter maltose was centrifuged for 15 min. at 10,000×g. The supernatant was precipitated with 1.5 liter of a saturated ammonium sulphate solution. The ammonium sulphate solution was added at a rate of 50 ml/min. under continuous stirring. The resulting 60% (w/v) ammonium sulphate solution was centrifuged for 15 min. at 10,000×g. The precipitate was resuspended in 10 ml of a sodium phosphate solution (10 mM, pH 6.0) and dialysed overnight against 10 mM sodium phosphate, pH 6.0.

A hydroxylapatite column was washed with a 10 mM sodium phosphate solution pH 6.0; the dialysed sample was loaded on the column. After eluting the column with 200 mM sodium phosphate, pH 6.0 the eluted fractions were screened for glucose releasing activity and fractions were pooled for phenyl superose (a hydrophobic interactions column) chromatography. The pooled fractions were diluted 1:1 (v:v) with 25 mM sodium acetate, 2 M ammonium sulphate, pH 5.4 and loaded on a phenyl superose column (washed with 25 mM sodium acetate, 1 M ammonium sulphate, pH 5.4). In a gradient from 25 mM sodium acetate, 1 M ammonium sulphate, pH 5.4 (A) to 25 mM sodium acetate, pH 5.4 (B) fractions were collected from 35% B to 50% B.

Pooled fractions from the phenyl superose column were loaded on a gel filtration (superdex) column and eluted by a 25 mM acetate, 0.1 M sodium chloride, pH 5.4 buffer. The superdex fractions were loaded on a washed (with 25 mM sodium acetate, pH 5.4) Mono Q column and eluted with 25 mM sodium acetate, 1 M sodium chloride, pH 5.4. The fractions containing glucose liberating activity were pooled, dialysed against 25 mM sodium acetate, pH 5.4, and stored at −20° C.

A levansucrase enzyme was purified from LB121 cultures grown on media containing maltose using ammonium sulfate precipitation and several chromatography column steps (table 2). Maltose (glucose—glucose) was chosen because both glucansucrase and levansucrase can not use maltose as substrate. LB121 will grow on media containing maltose but will not produce polysaccharide. From earlier experiments it was clear that even with harsh methods the levansucrase enzyme could not be separated from its product levan. These harsh methods included boiling the levan in a SDS solution and treating the levan with HCl and TFA. No levanase enzyme was commercially available for the enzymatic breakdown of levan. Only a single levansucrase was detected in maltose culture supernatants. In order to prove that the enzyme purified from maltose culture supernatant is the same enzyme which is responsible for the levan production during growth on raffinose, biochemical and biophysical tests were performed.

TABLE 2

Purification of the *Lactobacillus reuteri* LB 121 levansucrase (FTFB) enzyme

| Step | Protein (mg) | Total Activity (U) | Specific Activity (U/mg) | Purification (fold) | Yield (%) |
|---|---|---|---|---|---|
| Supernatant | 128 | 64 | 0.5 | 1 | 100 |
| Ammonium sulfate precipitation (65%) | 35.2 | 42 | 1.2 | 2.4 | 65.6 |
| Hydroxyl apatite | 1.5 | 30.6 | 20.4 | 40.8 | 47.8 |
| Phenyl superose | 0.27 | 23 | 85 | 170 | 36 |
| Gel Filtration | 0.055 | 10 | 182 | 360 | 16 |
| MonoQ | 0.0255 | 4 | 176 | 352 | 6 |

Amino Acid Sequencing of FTFB

A 5% SDS-PAA gel was allowed to "age" overnight in order to reduce the amount of reacting chemical groups in the gel. Reaction of chemicals in the PAA gel (TEMED and ammonium persulphate) with proteins can cause some undesired effects, such as N-terminal blocking of the protein, making it more difficult to determine the protein amino acid composition. 0.1 mM thioglycolic acid (scavenger to reduce the amount of reactive groups in the PAA gel material) was added to the running buffer during electrophoresis.

In order to determine the amino acid sequence of internal peptides of protein bands running in a SDS-PAA gel, protein containing bands were cut out of the PAA gel. After fractionating the protein by digestion with chymotrypsin the N-terminal amino acid sequences of the digested proteins were determined (below).

N-terminal sequencing was performed by Western blotting of the proteins from the PAA gel to an Immobilon PVDF membrane (Millipore/Waters Inc.) at 0.8 mA/cm$^2$ for 1 h. After staining the PVDF membrane with Coomassie Brilliant Blue without adding acetic acid (to reduce N-terminal blocking) and destaining with 50% methanol, the corresponding bands were cut out of the PVDF membrane for N-terminal amino acid sequence determination.

Amino acid sequence determination was performed by automated Edman degradation as described by Koningsberg and Steinman (1977) The proteins (third edition) volume 3, 1–178 (Neurath and Hill, eds.). The automated equipment for Edman degradation was an Applied Biosystems model 477A pulse-liquid sequenator described by Hewick et al. (1981), J. Biol. Chem. 15, 7990–7997 connected to a RP-HPLC unit (model 120A, Applied Biosystems) for amino acid identification.

The N-terminal sequence of the purified FTFB was determined and found to be: (A) Q V E S N N Y N G V A E V N T E R Q A N G Q I (G) (V) (D) (SEQ ID No. 6). Three internal peptide sequences of the purified FTFB were determined: (M) (A) H L D V W D S W P V Q D P (V) (SEQ ID No. 7); N A G S I F G T (K) (SEQ ID No. 8); and V (E) (E) V Y S P K V S T L M A S D E V E (SEQ ID No. 9).

The following primers were designed on the basis of the N-terminal and internal peptide fragments of FTFB. Listed from left to right are: primer name, source peptide fragment and sequence (from 5' to 3'). FTFB1+FTFB3i yields approximately a 1400 bp product in a PCR reaction. FTFB1 forward (N-terminal): AA T/C-TAT-AA T/C-GG T/C-GTT-GC G/A-T/C GA-AGT (SEQ ID No. 25); and FTFB3i reverse (Internal 3): TAC-CGN-A/T C/G N-CTA-CTT-CAA-CTT (SEQ ID No. 26). The FTFB gene was partly isolated by PCR with primers FTFB1 and FTFB3i. PCR with these primers yielded a 1385 bp amplicon, which after sequencing showed high homology to ftfA and SacB from *Streptococcus mutans*.

EXAMPLE 3

Oxidation of Levans

For TEMPO-mediated oxidation, a levan according to the invention prepared as described above (dry weight 1 g, 6.15 mmol) was resuspended in 100 ml water. Next, 2,2,6,6-tetramethylpiperidine-1-oxyl (TEMPO; 1% by weight compared to the polysaccharide (0.01 g, 0.065 mmol)) was added and resuspended in 20 min. Sodium bromide (0.75 g, 7.3 mmol) was added and the suspension was cooled down to 0° C. This reaction also proceded without bromide. A solution of hypochlorite (6 ml, 15% solution, 12.6 mmol) was adjusted to pH 10.0 with 3M HCl and cooled to 0° C. This solution was added to the suspension of the polysaccharide and TEMPO. The course of the reaction was followed by monitoring the consumption of sodium hydroxide solution, which is equivalent to the formation of uronic acid. After 30 min, 60 ml 0.1M NaOH was consumed. This amount corresponds to the formation of 97% uronic acid. Thereafter, the solution was poured out in 96% ethanol (comprising 70% of the volume of the solution) causing the product to precipitate. The white precipitate was centrifuged, resuspended in ethanol/water (70/30 v/v) and centrifuged again. Next, the precipitate was resuspended in 96% ethanol and centrifuged. The obtained product was dried at reduced pressure. The uronic acid content was determined by means of the uronic acid assay according to Blumenkrantz and Abdoe-Hansen (Anal. Biochem., 54

(1973), 484). A calibration curve was generated using polygalacturonic acid (5, 10, 15 and 20 μg). With this calibration curve the uronic acid content in a sample of 20 μg of the product was determined. The obtained result was a content of 95% uronic acid with a yield of 96%.

Partial Oxidation

For partial oxidation, a levan according to the invention (dry weight 2 g, 12.3 mmol) was resuspended in 25 ml water. Next, TEMPO (1% by weight compared to the polysaccharide (0.02 g, 0.13 mmol)) was added, resuspended in 20 min and cooled to 0° C. A solution of hypochlorite (1 ml, 15% solution, 2.1 mmol) was adjusted to pH 9.0 with 3M HCl and cooled down to 0° C. This solution was added to the suspension of the polysaccharide and TEMPO. Within 5 min the mixture became a solid gel.

EXAMPLE 4

Adhesion of *Lactobacillus reuteri* Strains to Caco-2 Cell Lines

The adhesion of *Lactobacillus reuteri* strains to Caco-2 cell lines was determined as described below. Firstly, a bacterial suspension was prepared as follows. *Lactobacillus reuteri* strains LB 121, 35–5, K24 and DSM20016 and *L. rhamnosus* LGG (a well known probiotic strain with good adhering properties) were cultured in MRS broth supplemented with 5 μl/ml of methyl-1,2-[$^3$H]-thymidine at 37° C. for 18–20 h before the adhesion assays. The cultures were harvested by centrifugation, washed with phosphate buffered saline (PBS) and resuspended in PBS or PBS supplemented with 30 g/l sucrose (see Table 3) to a final density of about $2 \times 10^9$ cfu/ml. Prior to the adhesion assay, the cell suspensions in PBS with 30 g/l sucrose were incubated for 1 hour at 37° C., whereas the cell suspensions in PBS were kept on ice for 1 hour. After incubation at 37° C., the suspensions in PBS with sucrose were centrifuged and the cells were washed with and resuspended in PBS to a final density of about $2 \times 10^9$ cfu/ml.

Caco-2 cells were cultured as follows. Subcultures of Caco-2 cells (ATCC, code HTB 37, human colon adenocarcinoma), stored as frozen stock cultures in liquid nitrogen were used for the adhesion tests. The Caco-2 cells were grown in culture medium consisting of Dulbecco's modified Eagle medium (DMEM), supplemented with heat-inactivated foetal calf serum (10% v/v), non-essential amino acids (1% v/v), L-glutamine (2 mM) and gentamicin (50 μg/ml). About 2,000,000 cells were seeded in 75 cm$^2$ tissue culture flasks containing culture medium and cultured in a humidified incubator at 37° C. in air containing 5% $CO_2$. Near confluent Caco-2 cell cultures were harvested by trypsinisation and resuspended in culture medium. The number of cells was established using a Bürker-Türk counting chamber.

TABLE 3

Incubation of the different Lactobacillus strains prior to the adhesion assays.

| Lactobacillus strain | Extra incubation | Polysaccharide produced | Group |
|---|---|---|---|
| reuteri 121 | PBS sucrose, 37° C. for 1 hr | glucan and fructan | As |
| reuteri 35-5 | PBS sucrose, 37° C. for 1 hr | glucan | Bs |
| reuteri K24 | PBS sucrose, 37° C. for 1 hr | none | Cs |

TABLE 3-continued

Incubation of the different Lactobacillus strains prior to the adhesion assays.

| Lactobacillus strain | Extra incubation | Polysaccharide produced | Group |
|---|---|---|---|
| reuteri 121 | PBS on ice | none | D |
| reuteri DSM20016* | PBS on ice | none | E |
| rhamnosus GG | PBS on ice | none | F |

*Type strain of L. reuteri

For the following experiments a Caco-2 monolayer transport system was used. Caco-2 cells cultured in a two-compartment transport system are commonly used to study the intestinal, epithelial permeability. In this system the Caco-2 cell differentiates into polarized columnar cells after reaching confluency. The Caco-2 system has been shown to simulate the passive and active transcellular tranport of electrolytes, sugars, amino acids and lipophilic compounds (Hillgren et al. 1995, Dulfer et al., 1996, Duizer et al., 1997). Also, a clear correlation between the in vivo absorption and the permeability across the monolayers of Caco-2 cells has been reported (Artursson and Karlsson, 1990). For the present transport studies, Caco-2 cells were seeded on semi-permeable filter inserts (12 wells Transwell plates, Costar) at ca. 100,000 cells per filter (growth area ±1 cm$^2$ containing 2.5 ml culture medium). The cells on the insert were cultured for 17 to 24 days at 37° C. in a humidified incubator containing 5% $CO_2$ in air. During this culture period the cells have been subjected to an enterocyte-like differentiation. Gentamycin was eliminated from the culture medium two days prior to the adhesion assays.

The adhesion assay was performed as follows. PBS was used as exposure medium. 25 μl of a bacterial suspension ($2 \times 10^9$ cfu/ml) were added to 0.5 ml medium. The apical side of the Caco-2 monolayers was incubated with the bacterial suspensions for 1 hour at 37° C. After incubation, remaining fluid was removed and the cells were washed three times with 1 ml PBS. Subsequently, the Caco-2 monolayers were digested overnight with 1 ml 0.1M NaOH, 1% SDS. The lysate was mixed with 10 ml Hionic Fluor scintillation liquid and the radioactivity was measured by liquid scintillation counting using a LKB/Wallac scintillation counter. As a control, the radioactivity of the bacterial suspensions was measured. For each test group, the percentage of bacteria attached to the monolayers was calculated. All adhesion tests were performed in quadruple. In Table 4 the results of the bacterial adhesion test to Caco-2 cellines are given. From the results can be concluded that the glucans and the fructans contribute to the adherence of *Lactobacillus reuteri* to Caco-2 cellines. This could indicate that *Lactobacillus reuteri* strains producing EPS possess improved probiotic characteristics or that *Lactobacillus reuteri* and its polysaccharides could function as an exellent symbiotic.

TABLE 4

The results of the bacterial adhesion test to Caco-2 cellines.

| Group (see Table 1) | 0% of bacteria bound to the monolayer |
|---|---|
| As | 6.5 |
| Bs | 5.7 |
| Cs | 1.8 |

TABLE 4-continued

The results of the bacterial adhesion test to Caco-2 cellines.

| Group (see Table 1) | 0% of bacteria bound to the monolayer |
| --- | --- |
| D | 2.3 |
| E | 0.9 |
| F | 1.3 |

DESCRIPTION OF THE FIGURES

FIG. 1: The nucleic acid (SEQ ID NO: 4) and deduced amino acid sequences (SEQ ID NOS 27 and 1) of the novel inulosucrase of *Lactobacillus reuteri*. Also encompassed within the figure is the comparison peptide (SEQ ID NO: 28). Furthermore, the designations and orientation (< for 3' to 5' and > for 5' to 3') of the primers and the restriction enzymes used for (inverse) PCR, are shown at the right hand side. Putative start codons (ATG, at positions 41 and 68) and stop codon (TAA, at position 2435) are shown in bold. The positions of the primers used for PCR are shown in bold/underlined. The NheI restriction sites (at positions 1154 and 2592) used for inverse PCR are underlined. The primers used and their exact positions in the inulosucrase sequence are shown in table 1. Starting at amino acid 690, the 20 PXX (residues 690-749 of SEQ ID NO: 1) repeats are underlined. At amino acid 755 the LPXTG (SEQ ID NO: 5) motif is underlined.

FIG. 2: Dendrogram of bacterial and plant fructosyltransferases. The horizontal distances are a measure for the difference at the amino acid sequence level. 10% difference is indicated by the upper bar. Bootstrap values (in percentages) are given at the root of each tree. Fructosyltransferases of Gram positive bacteria are indicated in the lower half of the figure (*B. staerothermophilus* SurB; *B. amyloliquefaciens* SacB; B. subtilis SacB; *S. mutans* SacB; *L. reuteri* FtfA (inulosucrase); *S. salivarius* Ftf). Plant fructosyltransferases are indicated in the middle part of the figure (*Cynara scolymus* Ss-1 ft; *Allium cepa* F-6 gft; *Hordeum vulgare* Sf-6 ft). Fructosyltransferases of Gram negative bacteria are shown in the upper part of the figure (*Z. mobilis* LevU; *Z. mobilis* SucE2; *Z mobilis* SacB; *E. amylovora* Lcs; *A. diazotrophicus*LsdA).

FIG. 3: The N-terminal (SEQ ID NO: 6) and three internal amino acid sequences (SEQ ID NOS 7-9) of the novel levansucrase of *Lactobacillus reuteri*.

FIG. 4: Parts of an alignment of the deduced amino acid sequences of some bacterial fructosyltransferase genes (SEQ ID NOS 29-40). Sequences in bold indicate the consensus sequences used to construct the degenerated primers 5 ftf, 6 ftfi and 12 ftfi. (*) indicates a position with a fully conserved amino acid residue. (:) indicates a position with a fully conserved 'strong' group: STA, NEQK, NHQK, NDEQ, QHRK, MILV, MILF, HY, FYW. (.) indicates a position with a fully conserved 'weaker' group: CSA, ATV, SAG, STNK, STPA, SGND, SNDEQK, NDEQHK, NEQHRK, FVLIM, HFY. Goups are according to the Pam250 residue weight matrix described by Altschul et al. (1990) J. Mol. Biol. 215, 403-410.

What is claimed is:

1. A process of producing a fructo-oligosaccharide or fructo-polysaccharide, having β(2-1) linked D-fructosyl units comprising forming a mixture by combining sucrose with at least one reaction partner selected from the group consisting of:
   a) a protein having fructosyltransferase activity, which exhibits at least 85% amino acid identity, as determined by a BLAST algorithm, with an amino acid sequence of SEQ ID No. 1, and
   b) a recombinant host cell containing one or more copies of a nucleic acid construct encoding for said protein (a) and capable of expressing said protein;
   wherein said reaction partner interacts with sucrose to produce a fructo-oligosaccharide or fructo-polysaccharide.

2. The process according to claim 1, wherein said protein is a recombinant protein.

3. A process according to claim 1, further comprising chemically modifying said frusto-oligosaccharide or frusto-polysaccharide by simultaneous 3- and 4-oxidation, 1-or 6-oxidation, phosphorylation, acylation, hydroxyalkylation, carboxymethylation or amino-alkylation of one or more anhydrofructose units, or by hydrolysis.

4. The process according to claim 1, further comprising adding a food or beverage composition to said mixture to obtain a prebiotic composition.

5. The process according to claim 1, further comprising adding to said mixture a Lactobacillus strain capable of producing an oligosaccharide or polysaccharide and optionally a food or beverage composition, to obtain a synbiotic composition.

6. A process of producing a fructo-oligosaccharide or fructo-polysaccharide, having β(2-1) linked D-fructosyl units comprising combining sucrose and a protein to form a mixture, said protein having fructosyltransferase activity, which exhibits at least 85% amino acid identity, as determined by a BLAST algorithm, with an amino acid sequence of SEQ ID No. 1, and
   interacting said sucrose with said protein to produce said fruco-oligosaccharide or fructo-polysaccharide.

7. A process for producing a fructo-oligosaccharide or fructo-polysaccharide, having β(2-6) linked D-fructosyl units comprising forming a mixture by combining sucrose with a reaction partner, wherein said reaction partner is a recombinant host cell containing one or more copies of a nucleic acid construct encoding for a protein having fructosyltransferase activity, which exhibits at least 85% amino acid identity, as determined by a BLAST algorithm, with an amino acid sequence of SEQ ID No. 11, and wherein said reaction partner interacts with sucrose to provide a fructo-oligosaccharide or fructo-polysaccharide.

8. A process according to claim 7, further comprising chemically modifying said fructo-oligosaccharide or fructo-polysaccharide by simultaneous 3- and 4-oxidation, 1-or 6-oxidation, phosphorylation, acylation, hydroxyalkylation, carboxymethylation or amino-alkylation of one or more anhydrofructose units, or by hydrolysis.

* * * * *

SEQUENCE LISTING

<160> NUMBER OF SEQ ID NOS: 40

Figure 5:
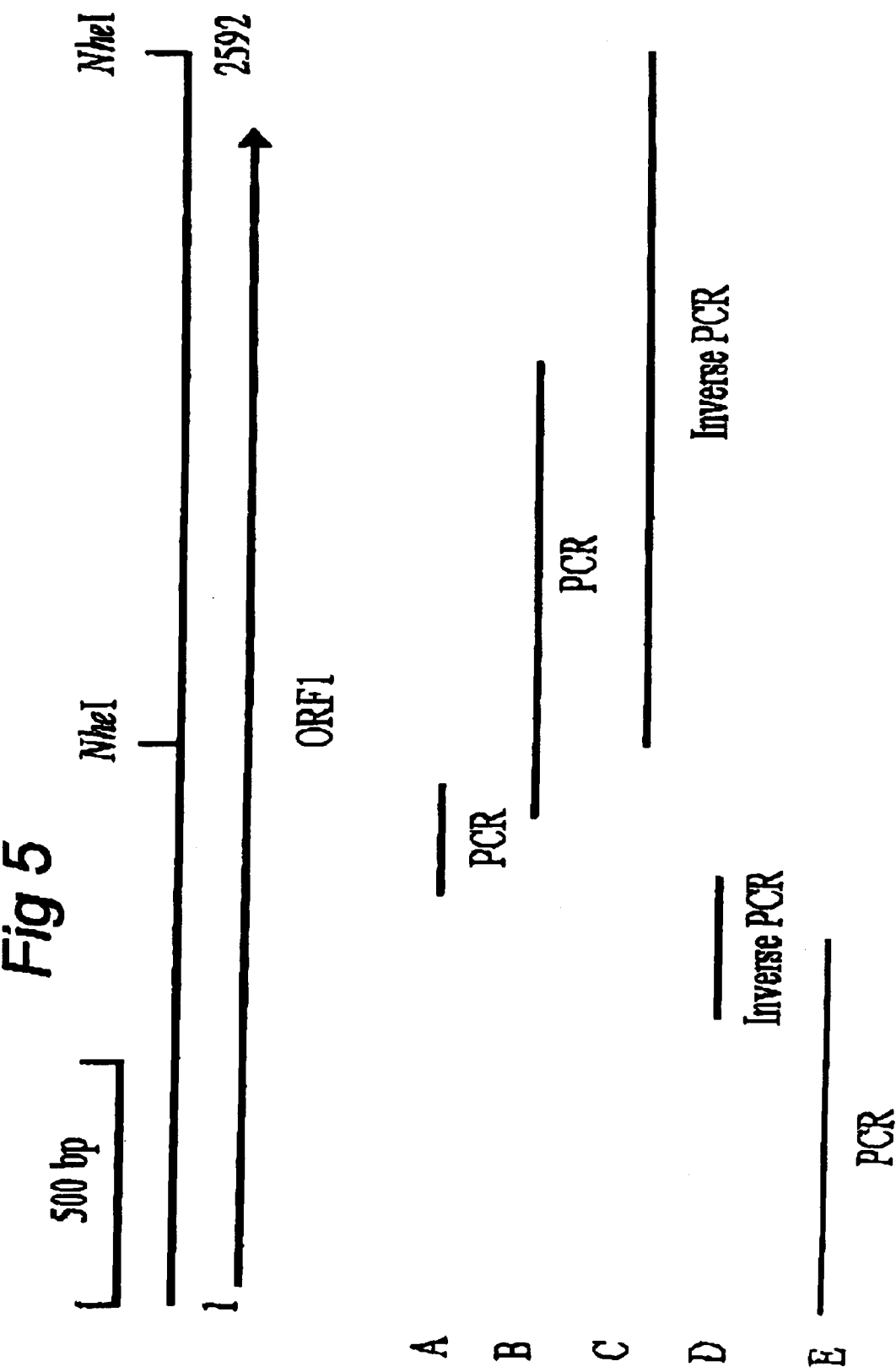
FIG. 5: The strategy used for the isolation of the inulosucrase gene from *Lactobacillus reuteri* 121 chromosomal DNA.

<210> SEQ ID NO 1
<211> LENGTH: 789
<212> TYPE: PRT
<213> ORGANISM: Lactobacillus reuteri

<400> SEQUENCE: 1

Met Tyr Lys Ser Gly Lys Asn Trp Ala Val Val Thr Leu Ser Thr Ala
 1               5                  10                  15

Ala Leu Val Phe Gly Ala Thr Thr Val Asn Ala Ser Ala Asp Thr Asn
                20                  25                  30

Ile Glu Asn Asn Asp Ser Ser Thr Val Gln Val Thr Thr Gly Asp Asn
            35                  40                  45

Asp Ile Ala Val Lys Ser Val Thr Leu Gly Ser Gly Gln Val Ser Ala
        50                  55                  60

Ala Ser Asp Thr Thr Ile Arg Thr Ser Ala Asn Ala Asn Ser Ala Ser
    65                  70                  75                  80

Ser Ala Ala Asn Thr Gln Asn Ser Asn Ser Gln Val Ala Ser Ser Ala
                85                  90                  95

Ala Ile Thr Ser Ser Thr Ser Ser Ala Ala Ser Leu Asn Asn Thr Asp
               100                 105                 110

Ser Lys Ala Ala Gln Glu Asn Thr Asn Thr Ala Lys Asn Asp Asp Thr
           115                 120                 125

Gln Lys Ala Ala Pro Ala Asn Glu Ser Ser Glu Ala Lys Asn Glu Pro

-continued

```
            130                 135                 140
Ala Val Asn Val Asn Asp Ser Ser Ala Ala Lys Asn Asp Asp Gln Gln
145                 150                 155                 160
Ser Ser Lys Lys Asn Thr Thr Ala Lys Leu Asn Lys Asp Ala Glu Asn
                165                 170                 175
Val Val Lys Lys Ala Gly Ile Asp Pro Asn Ser Leu Thr Asp Asp Gln
                180                 185                 190
Ile Lys Ala Leu Asn Lys Met Asn Phe Ser Lys Ala Ala Lys Ser Gly
                195                 200                 205
Thr Gln Met Thr Tyr Asn Asp Phe Gln Lys Ile Ala Asp Thr Leu Ile
                210                 215                 220
Lys Gln Asp Gly Arg Tyr Thr Val Pro Phe Phe Lys Ala Ser Glu Ile
225                 230                 235                 240
Lys Asn Met Pro Ala Ala Thr Thr Lys Asp Ala Gln Thr Asn Thr Ile
                245                 250                 255
Glu Pro Leu Asp Val Trp Asp Ser Trp Pro Val Gln Asp Val Arg Thr
                260                 265                 270
Gly Gln Val Ala Asn Trp Asn Gly Tyr Gln Leu Val Ile Ala Met Met
                275                 280                 285
Gly Ile Pro Asn Gln Asn Asp Asn His Ile Tyr Leu Leu Tyr Asn Lys
                290                 295                 300
Tyr Gly Asp Asn Glu Leu Ser His Trp Lys Asn Val Gly Pro Ile Phe
305                 310                 315                 320
Gly Tyr Asn Ser Thr Ala Val Ser Gln Glu Trp Ser Gly Ser Ala Val
                325                 330                 335
Leu Asn Ser Asp Asn Ser Ile Gln Leu Phe Tyr Thr Arg Val Asp Thr
                340                 345                 350
Ser Asp Asn Asn Thr Asn His Gln Lys Ile Ala Ser Ala Thr Leu Tyr
                355                 360                 365
Leu Thr Asp Asn Asn Gly Asn Val Ser Leu Ala Gln Val Arg Asn Asp
                370                 375                 380
Tyr Ile Val Phe Glu Gly Asp Gly Tyr Tyr Tyr Gln Thr Tyr Asp Gln
385                 390                 395                 400
Trp Lys Ala Thr Asn Lys Gly Ala Asp Asn Ile Ala Met Arg Asp Ala
                405                 410                 415
His Val Ile Glu Asp Gly Asn Gly Asp Arg Tyr Leu Val Phe Glu Ala
                420                 425                 430
Ser Thr Gly Leu Glu Asn Tyr Gln Gly Glu Asp Gln Ile Tyr Asn Trp
                435                 440                 445
Leu Asn Tyr Gly Gly Asp Asp Ala Phe Asn Ile Lys Ser Leu Phe Arg
                450                 455                 460
Ile Leu Ser Asn Asp Asp Ile Lys Ser Arg Ala Thr Trp Ala Asn Ala
465                 470                 475                 480
Ala Ile Gly Ile Leu Lys Leu Asn Lys Asp Glu Lys Asn Pro Lys Val
                485                 490                 495
Ala Glu Leu Tyr Ser Pro Leu Ile Ser Ala Pro Met Val Ser Asp Glu
                500                 505                 510
Ile Glu Arg Pro Asn Val Val Lys Leu Gly Asn Lys Tyr Tyr Leu Phe
                515                 520                 525
Ala Ala Thr Arg Leu Asn Arg Gly Ser Asn Asp Asp Ala Trp Met Asn
                530                 535                 540
Ala Asn Tyr Ala Val Gly Asp Asn Val Ala Met Val Gly Tyr Val Ala
545                 550                 555                 560
```

```
Asp Ser Leu Thr Gly Ser Tyr Lys Pro Leu Asn Asp Ser Gly Val Val
            565                 570                 575
Leu Thr Ala Ser Val Pro Ala Asn Trp Arg Thr Ala Thr Tyr Ser Tyr
        580                 585                 590
Tyr Ala Val Pro Val Ala Gly Lys Asp Asp Gln Val Leu Val Thr Ser
    595                 600                 605
Tyr Met Thr Asn Arg Asn Gly Val Ala Gly Lys Gly Met Asp Ser Thr
610                 615                 620
Trp Ala Pro Ser Phe Leu Leu Gln Ile Asn Pro Asp Asn Thr Thr Thr
625                 630                 635                 640
Val Leu Ala Lys Met Thr Asn Gln Gly Asp Trp Ile Trp Asp Asp Ser
            645                 650                 655
Ser Glu Asn Leu Asp Met Ile Gly Asp Leu Asp Ser Ala Ala Leu Pro
                660                 665                 670
Gly Glu Arg Asp Lys Pro Val Asp Trp Asp Leu Ile Gly Tyr Gly Leu
            675                 680                 685
Lys Pro His Asp Pro Ala Thr Pro Asn Asp Pro Glu Thr Pro Thr Thr
        690                 695                 700
Pro Glu Thr Pro Glu Thr Pro Asn Thr Pro Lys Thr Pro Lys Thr Pro
705                 710                 715                 720
Glu Asn Pro Gly Thr Pro Gln Thr Pro Asn Thr Pro Asn Thr Pro Glu
                725                 730                 735
Ile Pro Leu Thr Pro Glu Thr Pro Lys Gln Pro Glu Thr Gln Thr Asn
            740                 745                 750
Asn Arg Leu Pro Gln Thr Gly Asn Asn Ala Asn Lys Ala Met Ile Gly
        755                 760                 765
Leu Gly Met Gly Thr Leu Leu Ser Met Phe Gly Leu Ala Glu Ile Asn
    770                 775                 780
Lys Arg Arg Phe Asn
785

<210> SEQ ID NO 2
<211> LENGTH: 2367
<212> TYPE: DNA
<213> ORGANISM: Lactobacillus reuteri

<400> SEQUENCE: 2
atgtataaaa gcggtaaaaa ttgggcagtc gttacactct cgactgctgc gctggtattt      60
ggtgcaacaa ctgtaaatgc atccgcggac acaaatattg aaaacaatga ttcttctact     120
gtacaagtta caacaggtga taatgatatt gctgttaaaa gtgtgacact tggtagtggt     180
caagttagtg cagctagtga tacgactatt agaacttctg ctaatgcaaa tagtgcttct     240
tctgccgcta atacacaaaa ttctaacagt caagtagcaa gttctgctgc aataacatca     300
tctacaagtt ccgcagcttc attaaataac acagatagta agcggctcaa gaaaatact      360
aatacagcca aaaatgatga cacgcaaaaa gctgcaccag ctaacgaatc ttctgaagct     420
aaaaatgaac cagctgtaaa cgttaatgat tcttcagctg caaaaaatga tgatcaacaa     480
tccagtaaaa agaatactac cgctaagtta acaaggatg ctgaaaacgt tgtaaaaaag      540
gcgggaattg atcctaacag tttaactgat gaccagatta agcattaaa taagatgaac      600
ttctcgaaag ctgcaaagtc tggtacacaa atgacttata tgatttcca aaagattgct      660
gatacgttaa tcaaacaaga tggtcggtac acagttccat tctttaaagc aagtgaaatc     720
aaaaatatgc ctgccgctac aactaaagat gcacaaacta atactattga acctttagat     780
```

```
gtatgggatt catggccagt tcaagatgtt cggacaggac aagttgctaa ttggaatggc    840
tatcaacttg tcatcgcaat gatgggaatt ccaaaccaaa atgataatca tatctatctc    900
ttatataata agtatggtga taatgaatta agtcattgga agaatgtagg tccaattttt    960
ggctataatt ctaccgcggt ttcacaagaa tggtcaggat cagctgtttt gaacagtgat   1020
aactctatcc aattatttta tacaagggta gacacgtctg ataacaatac caatcatcaa   1080
aaaattgcta gcgctactct ttatttaact gataataatg gaaatgtatc actcgctcag   1140
gtacgaaatg actatattgt atttgaaggt gatggctatt actaccaaac ttatgatcaa   1200
tggaaagcta ctaacaaagg tgccgataat attgcaatgc gtgatgctca tgtaattgaa   1260
gatggtaatg gtgatcggta ccttgttttt gaagcaagta ctggtttgga aaattatcaa   1320
ggcgaggacc aaatttataa ctggttaaat tatggcggag atgacgcatt taatatcaag   1380
agcttattta gaattctttc caatgatgat attaagagtc gggcaacttg gctaatgca    1440 gctatcggta tcctcaaact aaataaggac gaaaagaatc ctaaggtggc agagttatac   1500
tcaccattaa tttctgcacc aatggtaagc gatgaaattg agcgaccaaa tgtagttaaa   1560
ttaggtaata aatattactt atttgccgct acccgtttaa atcgaggaag taatgatgat   1620
gcttggatga atgctaatta tgccgttggt gataatgttg caatggtcgg atatgttgct   1680
gatagtctaa ctggatctta aagccatta aatgattctg gagtagtctt gactgcttct   1740
gttcctgcaa actggcggac agcaacttat tcatatatg ctgtcccgt tgccggaaaa    1800 gatgaccaag tattagttac ttcatatatg actaatagaa atggagtagc gggtaaagga   1860
atggattcaa cttgggcacc gagtttctta ctacaaatta cccggataa cacaactact    1920 gttttagcta aaatgactaa tcaaggggat tggatttggg atgattcaag cgaaaatctt   1980
gatatgattg gtgatttaga ctccgctgct ttacctggcg aacgtgataa acctgttgat   2040
tgggacttaa ttggttatgg attaaaaccg catgatcctg ctacaccaaa tgatcctgaa   2100
acgccaacta caccagaaac ccctgagaca cctaatactc ccaaaacacc aaagactcct   2160
gaaaatcctg gacacctca aactcctaat acacctaata ctccggaaat tcctttaact   2220
ccagaaacgc ctaagcaacc tgaaacccaa actaataatc gtttgccaca aactggaaat   2280
aatgccaata aagccatgat tggcctaggt atgggaacat tgcttagtat gtttggtctt   2340
gcagaaatta acaaacgtcg atttaac                                       2367
```

<210> SEQ ID NO 3
<211> LENGTH: 2394
<212> TYPE: DNA
<213> ORGANISM: Lactobacillus reuteri

<400> SEQUENCE: 3

```
atgctagaac gcaaggaaca taaaaaaatg tataaaagcg gtaaaaattg ggcagtcgtt     60
acactctcga ctgctgcgct ggtatttggt gcaacaactg taaatgcatc cgcggacaca    120
aatattgaaa caatgattc ttctactgta caagttacaa caggtgataa tgatattgct    180
gttaaaagtg tgacacttgg tagtggtcaa gttagtgcag ctagtgatac gactattaga    240
acttctgcta atgcaaatag tgcttcttct gccgctaata cacaaaattc taacagtcaa    300
gtagcaagtt ctgctgcaat aacatcatct acaagttccg cagcttcatt aaataacaca    360
gatagtaaag cggctcaaga aaatactaat acagccaaaa atgatgacac gcaaaaagct    420
gcaccagcta acgaatcttc tgaagctaaa aatgaaccag ctgtaaacgt taatgattct    480
```

-continued

```
tcagctgcaa aaaatgatga tcaacaatcc agtaaaaaga atactaccgc taagttaaac      540
aaggatgctg aaaacgttgt aaaaaaggcg ggaattgatc ctaacagttt aactgatgac      600
cagattaaag cattaaataa gatgaacttc tcgaaagctg caaagtctgg tacacaaatg      660
acttataatg atttccaaaa gattgctgat acgttaatca aacaagatgg tcggtacaca      720
gttccattct ttaaagcaag tgaaatcaaa atatgcctg ccgctacaac taagatgca       780 caaactaata ctattgaacc tttagatgta tgggattcat ggccagttca agatgttcgg      840
acaggacaag ttgctaattg gaatggctat caacttgtca tcgcaatgat gggaattcca      900
aaccaaaatg ataatcatat ctatctctta tataataagt atggtgataa tgaattaagt      960
cattggaaga atgtaggtcc aattttggc tataattcta ccgcggtttc acaagaatgg      1020
tcaggatcag ctgttttgaa cagtgataac tctatccaat tattttatac aagggtagac      1080
acgtctgata caataccaa tcatcaaaaa attgctagcg ctactcttta tttaactgat      1140
aataatggaa atgtatcact cgctcaggta cgaaatgact atattgtatt tgaaggtgat      1200
ggctattact accaaactta tgatcaatgg aaagctacta caaaggtgc cgataatatt      1260 gcaatgcgtg atgctcatgt aattgaagat ggtaatggtg atcggtacct tgttttgaa      1320 gcaagtactg gtttggaaaa ttatcaaggc gaggaccaaa tttataactg gttaaattat      1380
ggcggagatg acgcatttaa tatcaagagc ttatttagaa ttcttttccaa tgatgatat      1440 aagagtcggg caacttgggc taatgcagct atcggtatcc tcaaactaaa taaggacgaa      1500
aagaatccta aggtggcaga gttatactca ccattaattt ctgcaccaat ggtaagcgat      1560
gaaattgagc gaccaaatgt agttaaatta ggtaataaat attacttatt tgccgctacc      1620
cgtttaaatc gaggaagtaa tgatgatgct tggatgaatg ctaattatgc cgttggtgat      1680
aatgttgcaa tggtcggata tgttgctgat agtctaactg gatcttataa gccattaaat      1740
gattctggag tagtcttgac tgcttctgtt cctgcaaact ggcggacagc aacttattca      1800
tattatgctg tccccgttgc cggaaaagat gaccaagtat tagttacttc atatatgact      1860
aatagaaatg gagtagcggg taaggaatg gattcaactt gggcaccgag tttcttacta      1920
caaattaacc cggataacac aactactgtt ttagctaaaa tgactaatca aggggattgg      1980
atttgggatg attcaagcga aaatcttgat atgattggtg atttagactc cgctgcttta      2040
cctggcgaac gtgataaacc tgttgattgg gacttaattg gttatggatt aaaaccgcat      2100
gatcctgcta caccaaatga tcctgaaacg ccaactacac cagaaacccc tgagacacct      2160
aatactccca aaacaccaaa gactcctgaa atcctgggaa caccctcaaac tcctaataca      2220 cctaatactc cggaaattcc tttaactcca gaaacgccta agcaacctga aacccaaact      2280
aataatcgtt tgccacaaac tggaaataat gccaataaag ccatgattgg cctaggtatg      2340
ggaacattgc ttagtatgtt tggtcttgca gaaattaaca aacgtcgatt taac           2394
```

<210> SEQ ID NO 4
<211> LENGTH: 2592
<212> TYPE: DNA
<213> ORGANISM: Lactobacillus reuteri
<220> FEATURE:
<221> NAME/KEY: CDS
<222> LOCATION: (1)..(51)
<220> FEATURE:
<221> NAME/KEY: CDS
<222> LOCATION: (68)..(2434)

<400> SEQUENCE: 4

```
tac aat ggg gtg gcg gag gtg aag aaa cgg ggt tac ttc tat gct aga        48
```

```
                Tyr Asn Gly Val Ala Glu Val Lys Lys Arg Gly Tyr Phe Tyr Ala Arg
                  1               5                  10                  15 acg caaggaacat aaaaaa atg tat aaa agc ggt aaa aat tgg gca gtc gtt        100
Thr                  Met Tyr Lys Ser Gly Lys Asn Trp Ala Val Val
                      20                          25 aca ctc tcg act gct gcg ctg gta ttt ggt gca aca act gta aat gca         148
Thr Leu Ser Thr Ala Ala Leu Val Phe Gly Ala Thr Thr Val Asn Ala
     30                  35                  40 tcc gcg gac aca aat att gaa aac aat gat tct tct act gta caa gtt         196
Ser Ala Asp Thr Asn Ile Glu Asn Asn Asp Ser Ser Thr Val Gln Val
 45                  50                  55                  60 aca aca ggt gat aat gat att gct gtt aaa agt gtg aca ctt ggt agt         244
Thr Thr Gly Asp Asn Asp Ile Ala Val Lys Ser Val Thr Leu Gly Ser
                 65                  70                  75 ggt caa gtt agt gca gct agt gat acg act att aga act tct gct aat         292
Gly Gln Val Ser Ala Ala Ser Asp Thr Thr Ile Arg Thr Ser Ala Asn
             80                  85                  90 gca aat agt gct tct tct gcc gct aat aca caa aat tct aac agt caa         340
Ala Asn Ser Ala Ser Ser Ala Ala Asn Thr Gln Asn Ser Asn Ser Gln
         95                 100                 105 gta gca agt tct gct gca ata aca tca tct aca agt tcc gca gct tca         388
Val Ala Ser Ser Ala Ala Ile Thr Ser Ser Thr Ser Ser Ala Ala Ser
    110                 115                 120 tta aat aac aca gat agt aaa gcg gct caa gaa aat act aat aca gcc         436
Leu Asn Asn Thr Asp Ser Lys Ala Ala Gln Glu Asn Thr Asn Thr Ala
125                 130                 135                 140 aaa aat gat gac acg caa aaa gct gca cca gct aac gaa tct tct gaa         484
Lys Asn Asp Asp Thr Gln Lys Ala Ala Pro Ala Asn Glu Ser Ser Glu
                145                 150                 155 gct aaa aat gaa cca gct gta aac gtt aat gat tct tca gct gca aaa         532
Ala Lys Asn Glu Pro Ala Val Asn Val Asn Asp Ser Ser Ala Ala Lys
            160                 165                 170 aat gat gat caa caa tcc agt aaa aag aat act acc gct aag tta aac         580
Asn Asp Asp Gln Gln Ser Ser Lys Lys Asn Thr Thr Ala Lys Leu Asn
        175                 180                 185 aag gat gct gaa aac gtt gta aaa aag gcg gga att gat cct aac agt         628
Lys Asp Ala Glu Asn Val Val Lys Lys Ala Gly Ile Asp Pro Asn Ser
    190                 195                 200 tta act gat gac cag att aaa gca tta aat aag atg aac ttc tcg aaa         676
Leu Thr Asp Asp Gln Ile Lys Ala Leu Asn Lys Met Asn Phe Ser Lys
205                 210                 215                 220 gct gca aag tct ggt aca caa atg act tat aat gat ttc caa aag att         724
Ala Ala Lys Ser Gly Thr Gln Met Thr Tyr Asn Asp Phe Gln Lys Ile
                225                 230                 235 gct gat acg tta atc aaa caa gat ggt cgg tac aca gtt cca ttc ttt         772
Ala Asp Thr Leu Ile Lys Gln Asp Gly Arg Tyr Thr Val Pro Phe Phe
            240                 245                 250 aaa gca agt gaa atc aaa aat atg cct gcc gct aca act aaa gat gca         820
Lys Ala Ser Glu Ile Lys Asn Met Pro Ala Ala Thr Thr Lys Asp Ala
        255                 260                 265 caa act aat act att gaa cct tta gat gta tgg gat tca tgg cca gtt         868
Gln Thr Asn Thr Ile Glu Pro Leu Asp Val Trp Asp Ser Trp Pro Val
    270                 275                 280 caa gat gtt cgg aca gga caa gtt gct aat tgg aat ggc tat caa ctt         916
Gln Asp Val Arg Thr Gly Gln Val Ala Asn Trp Asn Gly Tyr Gln Leu
285                 290                 295                 300 gtc atc gca atg atg gga att cca aac caa aat gat aat cat atc tat         964
Val Ile Ala Met Met Gly Ile Pro Asn Gln Asn Asp Asn His Ile Tyr
                305                 310                 315
```

```
ctc tta tat aat aag tat ggt gat aat gaa tta agt cat tgg aag aat      1012
Leu Leu Tyr Asn Lys Tyr Gly Asp Asn Glu Leu Ser His Trp Lys Asn
            320                 325                 330 gta ggt cca att ttt ggc tat aat tct acc gcg gtt tca caa gaa tgg      1060
Val Gly Pro Ile Phe Gly Tyr Asn Ser Thr Ala Val Ser Gln Glu Trp
        335                 340                 345 tca gga tca gct gtt ttg aac agt gat aac tct atc caa tta ttt tat      1108
Ser Gly Ser Ala Val Leu Asn Ser Asp Asn Ser Ile Gln Leu Phe Tyr
350                 355                 360 aca agg gta gac acg tct gat aac aat acc aat cat caa aaa att gct      1156
Thr Arg Val Asp Thr Ser Asp Asn Asn Thr Asn His Gln Lys Ile Ala
365                 370                 375                 380 agc gct act ctt tat tta act gat aat aat gga aat gta tca ctc gct      1204
Ser Ala Thr Leu Tyr Leu Thr Asp Asn Asn Gly Asn Val Ser Leu Ala
            385                 390                 395 cag gta cga aat gac tat att gta ttt gaa ggt gat ggc tat tac tac      1252
Gln Val Arg Asn Asp Tyr Ile Val Phe Glu Gly Asp Gly Tyr Tyr Tyr
        400                 405                 410 caa act tat gat caa tgg aaa gct act aac aaa ggt gcc gat aat att      1300
Gln Thr Tyr Asp Gln Trp Lys Ala Thr Asn Lys Gly Ala Asp Asn Ile
    415                 420                 425 gca atg cgt gat gct cat gta att gaa gat ggt aat ggt gat cgg tac      1348
Ala Met Arg Asp Ala His Val Ile Glu Asp Gly Asn Gly Asp Arg Tyr
430                 435                 440 ctt gtt ttt gaa gca agt act ggt ttg gaa aat tat caa ggc gag gac      1396
Leu Val Phe Glu Ala Ser Thr Gly Leu Glu Asn Tyr Gln Gly Glu Asp
445                 450                 455                 460 caa att tat aac tgg tta aat tat ggc gga gat gac gca ttt aat atc      1444
Gln Ile Tyr Asn Trp Leu Asn Tyr Gly Gly Asp Asp Ala Phe Asn Ile
            465                 470                 475 aag agc tta ttt aga att ctt tcc aat gat gat att aag agt cgg gca      1492
Lys Ser Leu Phe Arg Ile Leu Ser Asn Asp Asp Ile Lys Ser Arg Ala
        480                 485                 490 act tgg gct aat gca gct atc ggt atc ctc aaa cta aat aag gac gaa      1540
Thr Trp Ala Asn Ala Ala Ile Gly Ile Leu Lys Leu Asn Lys Asp Glu
    495                 500                 505 aag aat cct aag gtg gca gag tta tac tca cca tta att tct gca cca      1588
Lys Asn Pro Lys Val Ala Glu Leu Tyr Ser Pro Leu Ile Ser Ala Pro
510                 515                 520 atg gta agc gat gaa att gag cga cca aat gta gtt aaa tta ggt aat      1636
Met Val Ser Asp Glu Ile Glu Arg Pro Asn Val Val Lys Leu Gly Asn
525                 530                 535                 540 aaa tat tac tta ttt gcc gct acc cgt tta aat cga gga agt aat gat      1684
Lys Tyr Tyr Leu Phe Ala Ala Thr Arg Leu Asn Arg Gly Ser Asn Asp
            545                 550                 555 gat gct tgg atg aat gct aat tat gcc gtt ggt gat aat gtt gca atg      1732
Asp Ala Trp Met Asn Ala Asn Tyr Ala Val Gly Asp Asn Val Ala Met
        560                 565                 570 gtc gga tat gtt gct gat agt cta act gga tct tat aag cca tta aat      1780
Val Gly Tyr Val Ala Asp Ser Leu Thr Gly Ser Tyr Lys Pro Leu Asn
    575                 580                 585 gat tct gga gta gtc ttg act gct tct gtt cct gca aac tgg cgg aca      1828
Asp Ser Gly Val Val Leu Thr Ala Ser Val Pro Ala Asn Trp Arg Thr
590                 595                 600 gca act tat tca tat tat gct gtc ccc gtt gcc gga aaa gat gac caa      1876
Ala Thr Tyr Ser Tyr Tyr Ala Val Pro Val Ala Gly Lys Asp Asp Gln
605                 610                 615                 620 gta tta gtt act tca tat atg act aat aga aat gga gta gcg ggt aaa      1924
Val Leu Val Thr Ser Tyr Met Thr Asn Arg Asn Gly Val Ala Gly Lys
            625                 630                 635
```

```
gga atg gat tca act tgg gca ccg agt ttc tta cta caa att aac ccg    1972
Gly Met Asp Ser Thr Trp Ala Pro Ser Phe Leu Leu Gln Ile Asn Pro
            640                 645                 650 gat aac aca act act gtt tta gct aaa atg act aat caa ggg gat tgg    2020
Asp Asn Thr Thr Thr Val Leu Ala Lys Met Thr Asn Gln Gly Asp Trp
        655                 660                 665 att tgg gat gat tca agc gaa aat ctt gat atg att ggt gat tta gac    2068
Ile Trp Asp Asp Ser Ser Glu Asn Leu Asp Met Ile Gly Asp Leu Asp
    670                 675                 680 tcc gct gct tta cct ggc gaa cgt gat aaa cct gtt gat tgg gac tta    2116
Ser Ala Ala Leu Pro Gly Glu Arg Asp Lys Pro Val Asp Trp Asp Leu
685                 690                 695                 700 att ggt tat gga tta aaa ccg cat gat cct gct aca cca aat gat cct    2164
Ile Gly Tyr Gly Leu Lys Pro His Asp Pro Ala Thr Pro Asn Asp Pro
            705                 710                 715 gaa acg cca act aca cca gaa acc cct gag aca cct aat act ccc aaa    2212
Glu Thr Pro Thr Thr Pro Glu Thr Pro Glu Thr Pro Asn Thr Pro Lys
        720                 725                 730 aca cca aag act cct gaa aat cct ggg aca cct caa act cct aat aca    2260
Thr Pro Lys Thr Pro Glu Asn Pro Gly Thr Pro Gln Thr Pro Asn Thr
    735                 740                 745 cct aat act ccg gaa att cct tta act cca gaa acg cct aag caa cct    2308
Pro Asn Thr Pro Glu Ile Pro Leu Thr Pro Glu Thr Pro Lys Gln Pro
750                 755                 760 gaa acc caa act aat aat cgt ttg cca caa act gga aat aat gcc aat    2356
Glu Thr Gln Thr Asn Asn Arg Leu Pro Gln Thr Gly Asn Asn Ala Asn
765                 770                 775                 780 aaa gcc atg att ggc cta ggt atg gga aca ttg ctt agt atg ttt ggt    2404
Lys Ala Met Ile Gly Leu Gly Met Gly Thr Leu Leu Ser Met Phe Gly
            785                 790                 795 ctt gca gaa att aac aaa cgt cga ttt aac taaatacttt aaaataaaac     2454
Leu Ala Glu Ile Asn Lys Arg Arg Phe Asn
        800                 805 cgctaagcct taaattcagc ttaacggttt tttattttaa aagtttttat tgtaaaaaag  2514
cgaattatca ttaatactaa tgcaattgtt gtaagacctt acgacagtag taacaatgaa  2574
tttgcccatc tttgtcgg                                                2592

<210> SEQ ID NO 5
<211> LENGTH: 5
<212> TYPE: PRT
<213> ORGANISM: Lactobacillus reuteri
<220> FEATURE:
<221> NAME/KEY: MOD_RES
<222> LOCATION: (3)
<223> OTHER INFORMATION: Any amino acid

<400> SEQUENCE: 5

Leu Pro Xaa Thr Gly
  1               5

<210> SEQ ID NO 6
<211> LENGTH: 27
<212> TYPE: PRT
<213> ORGANISM: Lactobacillus reuteri

<400> SEQUENCE: 6

Ala Gln Val Glu Ser Asn Asn Tyr Asn Gly Val Ala Glu Val Asn Thr
  1               5                  10                  15

Glu Arg Gln Ala Asn Gly Gln Ile Gly Val Asp
                20                  25
```

<210> SEQ ID NO 7
<211> LENGTH: 16
<212> TYPE: PRT
<213> ORGANISM: Lactobacillus reuteri

<400> SEQUENCE: 7

Met Ala His Leu Asp Val Trp Asp Ser Trp Pro Val Gln Asp Pro Val
 1               5                  10                  15

<210> SEQ ID NO 8
<211> LENGTH: 9
<212> TYPE: PRT
<213> ORGANISM: Lactobacillus reuteri

<400> SEQUENCE: 8

Asn Ala Gly Ser Ile Phe Gly Thr Lys
 1               5

<210> SEQ ID NO 9
<211> LENGTH: 19
<212> TYPE: PRT
<213> ORGANISM: Lactobacillus reuteri

<400> SEQUENCE: 9

Val Glu Glu Val Tyr Ser Pro Lys Val Ser Thr Leu Met Ala Ser Asp
 1               5                  10                  15

Glu Val Glu

<210> SEQ ID NO 10
<211> LENGTH: 4634
<212> TYPE: DNA
<213> ORGANISM: Lactobacillus reuteri
<220> FEATURE:
<221> NAME/KEY: CDS
<222> LOCATION: (1220)..(3598)
<220> FEATURE:
<221> NAME/KEY: RBS
<222> LOCATION: (1205)..(1210)
<220> FEATURE:
<221> NAME/KEY: modified_base
<222> LOCATION: (2702)..(2707)
<223> OTHER INFORMATION: a, c, t, g, other or unknown
<220> FEATURE:
<221> NAME/KEY: modified_base
<222> LOCATION: (3686)..(3698)
<223> OTHER INFORMATION: a, c, t, g, other or unknown

<400> SEQUENCE: 10
gttaacaaag acaaaatttt atataattct tcaaattaaa tttcccactg taagaacata      60
aatgggtacc tgtttgatgg aataatata tttgtaacta accggccggc acctctttct     120
aatgtgccta ggatgcataa tggatgtaaa ttactagatg gcggttttta tacattaacc     180
tcgcaggaga gaaaagaagc aattagtaag gatccatatg cagataaatt tattaggcct     240
tatttaggtg ctaaaaattt cattcatgga actgctaggt actgtatttg gttaaaggac     300
gcaaacccga agatatcca tcaatcgcca tttatactgg atagaatcaa taagtagcg      360 gaattcagat cgcagcaaaa aagtaaagat acacaaaaat atgcaaaacg gcccatgcta     420
acaacacgac ttgcctatta tagccacgat gtacatacgg atatgctgat agtacctgca     480
acatcatcgc aacgtagaga atatcttcca attggatatg tttcagaaaa gaatattgtg     540
tcttattcac taatgctaat ccccaatgct agtaatttta atttcggtat tctagaatct     600
aaagttcact atatttggtt aaaaaacttt tgcggtcggt tgaagtccga ttatcgttat     660

```
tcaaacacta ttatttataa taatttccct tggccgactg ttggtgacaa gccaggamca    720
acaccatctc tgacactcgc tcaaggtata ttaaatactc gcaagctcta tccagacagc    780
tcactggctg atctttatga tccactaaca atgccragtt gaactcgtaa agctcatgaa    840
gccaatgata aagctgttct taaagcatat ggattgagcc ctaaagctac tgagcaagaa    900
atcgtagaac atctatttaa gatgtatgaa aaactgacta aggtgaaag ataactttgt     960 aaaaccaata ttttataaag acagtaaatg ttaatttgat aaaacatat atttaataaa    1020 caaaagtgat ataatcaagt agttcttgt attacaaaat acatttaata tctctcagca    1080
ttttgcatac tgggagattt tttattgaca aattgtttga agtgcttat gatgaaaccg    1140 tgtagaaact aattcaattt gataaacgtt agacatttct gaggaggaag tcattttgga   1200
gtacaaagaa cataagaaa atg tat aaa gtc ggc aag aat tgg gcc gtt gct   1252
                    Met Tyr Lys Val Gly Lys Asn Trp Ala Val Ala
                     1               5                  10 aca ttg gta tca gct tca att tta atg gga ggg gtt gta acc gct cat    1300
Thr Leu Val Ser Ala Ser Ile Leu Met Gly Gly Val Val Thr Ala His
             15                  20                  25 gct gat caa gta gaa agt aac aat tac aac ggt gtt gct gaa gtt aat    1348
Ala Asp Gln Val Glu Ser Asn Asn Tyr Asn Gly Val Ala Glu Val Asn
         30                  35                  40 act gaa cgt caa gct aat ggt caa att ggc gta gat gga aaa att att    1396
Thr Glu Arg Gln Ala Asn Gly Gln Ile Gly Val Asp Gly Lys Ile Ile
     45                  50                  55 agt gct aac agt aat aca acc agt ggc tcg aca aat caa gaa tca tct    1444
Ser Ala Asn Ser Asn Thr Thr Ser Gly Ser Thr Asn Gln Glu Ser Ser
 60                  65                  70                  75 gct act aac aat act gaa aat gct gtt gtt aat gaa agc aaa aat act    1492
Ala Thr Asn Asn Thr Glu Asn Ala Val Val Asn Glu Ser Lys Asn Thr
                 80                  85                  90 aac aat act gaa aat gct gtt gtt aat gaa aac aaa aat act aac aat    1540
Asn Asn Thr Glu Asn Ala Val Val Asn Glu Asn Lys Asn Thr Asn Asn
             95                 100                 105 act gaa aat gct gtt gtt aat gaa aac aaa aat act aac aac aca gaa    1588
Thr Glu Asn Ala Val Val Asn Glu Asn Lys Asn Thr Asn Asn Thr Glu
        110                 115                 120 aac gat aat agt caa tta aag tta act aat aat gaa caa cca tca gcc    1636
Asn Asp Asn Ser Gln Leu Lys Leu Thr Asn Asn Glu Gln Pro Ser Ala
    125                 130                 135 gct act caa gca aac ttg aag aag cta aat cct caa gct gct aag gct    1684
Ala Thr Gln Ala Asn Leu Lys Lys Leu Asn Pro Gln Ala Ala Lys Ala
140                 145                 150                 155 gtt caa aat gcc aag att gat gcc ggt agt tta aca gat gat caa att    1732
Val Gln Asn Ala Lys Ile Asp Ala Gly Ser Leu Thr Asp Asp Gln Ile
                160                 165                 170 aat gaa tta aat aag att aac ttc tct aag tct gct gaa aag ggt gca    1780
Asn Glu Leu Asn Lys Ile Asn Phe Ser Lys Ser Ala Glu Lys Gly Ala
            175                 180                 185 aaa ttg acc ttt aag gac tta gag ggg att ggt aat gct att gtt aag    1828
Lys Leu Thr Phe Lys Asp Leu Glu Gly Ile Gly Asn Ala Ile Val Lys
        190                 195                 200 caa gat cca caa tat gct att cct tat tct aat gct aag gaa atc aag    1876
Gln Asp Pro Gln Tyr Ala Ile Pro Tyr Ser Asn Ala Lys Glu Ile Lys
    205                 210                 215 aat atg cct gca aca tac act gta gat gcc caa aca ggt aag atg gct    1924
Asn Met Pro Ala Thr Tyr Thr Val Asp Ala Gln Thr Gly Lys Met Ala
220                 225                 230                 235
```

```
cat ctt gat gtc tgg gac tct tgg cca gta caa gat cct gtc aca ggt    1972
His Leu Asp Val Trp Asp Ser Trp Pro Val Gln Asp Pro Val Thr Gly
            240                 245                 250 tat gta tct aat tac atg ggt tat caa cta gtt att gct atg atg ggt    2020
Tyr Val Ser Asn Tyr Met Gly Tyr Gln Leu Val Ile Ala Met Met Gly
        255                 260                 265 att cca aat tcg cca act gga gat aat cat atc tat ctt ctt tac aac    2068
Ile Pro Asn Ser Pro Thr Gly Asp Asn His Ile Tyr Leu Leu Tyr Asn
    270                 275                 280 aag tat ggt gat aat gac ttt tct cat tgg cgc aat gca ggt tca atc    2116
Lys Tyr Gly Asp Asn Asp Phe Ser His Trp Arg Asn Ala Gly Ser Ile
285                 290                 295 ttt gga act aaa gaa aca aat gtg ttc caa gaa tgg tca ggt tca gct    2164
Phe Gly Thr Lys Glu Thr Asn Val Phe Gln Glu Trp Ser Gly Ser Ala
300                 305                 310                 315 att gta aat gat gat ggt aca att caa cta ttt ttc acc tca aat gat    2212
Ile Val Asn Asp Asp Gly Thr Ile Gln Leu Phe Phe Thr Ser Asn Asp
        320                 325                 330 acg tct gat tac aag ttg aat gat caa cgc ctt gct acc gca aca tta    2260
Thr Ser Asp Tyr Lys Leu Asn Asp Gln Arg Leu Ala Thr Ala Thr Leu
            335                 340                 345 aac ctt aat gtt gat gat aac ggt gtt tca atc aag agt gtt gat aat    2308
Asn Leu Asn Val Asp Asp Asn Gly Val Ser Ile Lys Ser Val Asp Asn
                350                 355                 360 tat caa gtt ttg ttt gaa ggt gat gga ttt cac tac caa act tat gaa    2356
Tyr Gln Val Leu Phe Glu Gly Asp Gly Phe His Tyr Gln Thr Tyr Glu
365                 370                 375 caa ttc gca aac ggc aaa gat cgt gaa aat gat gat tac tgc tta cgt    2404
Gln Phe Ala Asn Gly Lys Asp Arg Glu Asn Asp Asp Tyr Cys Leu Arg
380                 385                 390                 395 gac cca cac gtt gtt caa tta gaa aat ggt gat cgt tat ctt gta ttc    2452
Asp Pro His Val Val Gln Leu Glu Asn Gly Asp Arg Tyr Leu Val Phe
        400                 405                 410 gaa gct aat act ggg aca gaa gat tac caa agt gac gac caa att tat    2500
Glu Ala Asn Thr Gly Thr Glu Asp Tyr Gln Ser Asp Asp Gln Ile Tyr
            415                 420                 425 aat tgg gct aac tat ggt ggc gat gat gcc ttc aat att aag agt tcc    2548
Asn Trp Ala Asn Tyr Gly Gly Asp Asp Ala Phe Asn Ile Lys Ser Ser
                430                 435                 440 ttc aag ctt ttg aat aat aag aag gat cgt gaa ttg gct ggt tta gct    2596
Phe Lys Leu Leu Asn Asn Lys Lys Asp Arg Glu Leu Ala Gly Leu Ala
445                 450                 455 aat ggt gca ctt ggt atc tta aag ctc act aac aat caa agt aag cca    2644
Asn Gly Ala Leu Gly Ile Leu Lys Leu Thr Asn Asn Gln Ser Lys Pro
460                 465                 470                 475 aag gtt gaa gaa gta tac tca cca ttg gta tct act ttg atg gct tgc    2692
Lys Val Glu Glu Val Tyr Ser Pro Leu Val Ser Thr Leu Met Ala Cys
        480                 485                 490 gat gag gta nnn nnn aag ctt ggt gat aag tat tat ctc ttc tcc gta    2740
Asp Glu Val Xaa Xaa Lys Leu Gly Asp Lys Tyr Tyr Leu Phe Ser Val
            495                 500                 505 act cgt gta agt cgt ggt tcc gat cgt gaa tta acc gct aag gat aac    2788
Thr Arg Val Ser Arg Gly Ser Asp Arg Glu Leu Thr Ala Lys Asp Asn
                510                 515                 520 aca atc gtt ggt gat aac gtt gct atg att ggt tac gtt tcc gat agc    2836
Thr Ile Val Gly Asp Asn Val Ala Met Ile Gly Tyr Val Ser Asp Ser
525                 530                 535 tta atg ggt aag tac aag cca tta aat aac tca ggt gtc gta tta act    2884
Leu Met Gly Lys Tyr Lys Pro Leu Asn Asn Ser Gly Val Val Leu Thr
540                 545                 550                 555
```

| | | |
|---|---|---|
| gca tca gta cct gca aac tgg cgt act gct act tat tcc tac tat gca<br>Ala Ser Val Pro Ala Asn Trp Arg Thr Ala Thr Tyr Ser Tyr Tyr Ala<br>560 565 570 | | 2932 |
| gta cct gta gct ggt cat cct gat caa gta tta att act tct tac atg<br>Val Pro Val Ala Gly His Pro Asp Gln Val Leu Ile Thr Ser Tyr Met<br>575 580 585 | | 2980 |
| agt aac aag gac ttt gct tca ggt gaa gga aac tat gca act tgg gca<br>Ser Asn Lys Asp Phe Ala Ser Gly Glu Gly Asn Tyr Ala Thr Trp Ala<br>590 595 600 | | 3028 |
| cca agt ttc tta gta caa atc aat cca gat gac acg aca act gta tta<br>Pro Ser Phe Leu Val Gln Ile Asn Pro Asp Asp Thr Thr Thr Val Leu<br>605 610 615 | | 3076 |
| gca cgt gca act aac caa ggt gac tgg gtg tgg gac gac tct agt cgg<br>Ala Arg Ala Thr Asn Gln Gly Asp Trp Val Trp Asp Asp Ser Ser Arg<br>620 625 630 635 | | 3124 |
| aac gat aat atg ctc ggt gtt ctt aaa gaa ggt gca gct aac agt gcc<br>Asn Asp Asn Met Leu Gly Val Leu Lys Glu Gly Ala Ala Asn Ser Ala<br>640 645 650 | | 3172 |
| gcc tta cca ggt gaa tgg ggt aag cca gtt gac tgg agt ttg att aac<br>Ala Leu Pro Gly Glu Trp Gly Lys Pro Val Asp Trp Ser Leu Ile Asn<br>655 660 665 | | 3220 |
| aga agt cct ggc tta ggc tta aag cct cat caa cca gtt caa cca aag<br>Arg Ser Pro Gly Leu Gly Leu Lys Pro His Gln Pro Val Gln Pro Lys<br>670 675 680 | | 3268 |
| att gat caa cct gat caa caa cct tct ggt caa aac act aag aat gtc<br>Ile Asp Gln Pro Asp Gln Gln Pro Ser Gly Gln Asn Thr Lys Asn Val<br>685 690 695 | | 3316 |
| aca cca ggt aat ggt gat aag cct gct ggt aag gca act cct gat aac<br>Thr Pro Gly Asn Gly Asp Lys Pro Ala Gly Lys Ala Thr Pro Asp Asn<br>700 705 710 715 | | 3364 |
| act aat att gat cca agt gca caa cct tct ggt caa aac act aat att<br>Thr Asn Ile Asp Pro Ser Ala Gln Pro Ser Gly Gln Asn Thr Asn Ile<br>720 725 730 | | 3412 |
| gat cca agt gca caa mct tct ggt caa aac act aag aat gtc aca cca<br>Asp Pro Ser Ala Gln Xaa Ser Gly Gln Asn Thr Lys Asn Val Thr Pro<br>735 740 745 | | 3460 |
| ggt aat gag aaa caa ggt aag aat acc gat gca aaa caa tta cca caa<br>Gly Asn Glu Lys Gln Gly Lys Asn Thr Asp Ala Lys Gln Leu Pro Gln<br>750 755 760 | | 3508 |
| aca ggt aat aag tct ggt tta gca gga ctt tac gct ggt tca tta ctt<br>Thr Gly Asn Lys Ser Gly Leu Ala Gly Leu Tyr Ala Gly Ser Leu Leu<br>765 770 775 | | 3556 |
| gcc ttg ttt gga ttg gca gca att gaa aag cgt cac gct taa<br>Ala Leu Phe Gly Leu Ala Ala Ile Glu Lys Arg His Ala<br>780 785 790 | | 3598 |
| tagagtaaaa aaacatcctc cactcaagtt acaagtagga taatatgtat tatttctacg | | 3658 |
| cytagtcaag aggrattact ggacatannn nnnnnnnnnn tccagttacc aagtggaata | | 3718 |
| tagtattatt ccacgctagt caggaggatt actgacatta ttggctacat ggccggtagt | | 3778 |
| cctcttttct tttgtgacga attgtcaaac caagtgcaac ggtttctcaa aaacacctc | | 3838 |
| atatggggtt tcataattta acacttttcg aggacggcgg ttcagctgat gttggcagaa | | 3898 |
| actgacgtcc ttatctgtat aatcatcaat attagcccctt ttaggaaagt attccctaat | | 3958 |
| tagsccattg gtatttcat tgggtcctct ttcctctggt gaatagggat ctggccaata | | 4018 |
| gatagctact cctaaacgtc ctcgaatatc attcaagcca agaaattcac gcccatgatc | | 4078 |
| tggagtcaat gaatggacaa attctttagg aatagaccct aagagatcaa ttaagccctg | | 4138 |

-continued

```
atatttgaat tcggagaagg ggagttgtcc aacaattgcc gttataatac cagggttaat    4198
acggccctgg gcctctacgg taatattgta ttttggctc agatcagtga tagaaaccca     4258
cagatttagc ttgccggtgg agtgctgctt gaagtcttca attacttcgt taccatgttt    4318
gattgctaat ctgatgtgtc gttgttgtgg tgtagtaggc atcataccac ctcctcataa    4378
aataaggtat aacaggaatt tcttgtacta tatgatcctt ccaatataat aatattaggc    4438
cgataagaaa tgaccagcta ccatttcttg atgcttagtg aatataatcg gatgatacgt    4498 caccccctcaa caatccaatt tcacggaggt gagtaatcat gccgagagct aggaatgatt   4558
ggaggaacga acacggtcca tgcggcagtg gctatttgga ttttagccaa agcagcgtta    4618
ctgcttgcaa aagctt                                                    4634
```

```
<210> SEQ ID NO 11
<211> LENGTH: 792
<212> TYPE: PRT
<213> ORGANISM: Lactobacillus reuteri
<220> FEATURE:
<221> NAME/KEY: MOD_RES
<222> LOCATION: (495)..(496)
<223> OTHER INFORMATION: Any amino acid
<220> FEATURE:
<221> NAME/KEY: MOD_RES
<222> LOCATION: (737)
<223> OTHER INFORMATION: Thr or Pro

<400> SEQUENCE: 11

Met Tyr Lys Val Gly Lys Asn Trp Ala Val Ala Thr Leu Val Ser Ala
 1               5                  10                  15

Ser Ile Leu Met Gly Gly Val Val Thr Ala His Ala Asp Gln Val Glu
                20                  25                  30

Ser Asn Asn Tyr Asn Gly Val Ala Glu Val Asn Thr Glu Arg Gln Ala
            35                  40                  45

Asn Gly Gln Ile Gly Val Asp Gly Lys Ile Ile Ser Ala Asn Ser Asn
        50                  55                  60

Thr Thr Ser Gly Ser Thr Asn Gln Glu Ser Ser Ala Thr Asn Asn Thr
 65                  70                  75                  80

Glu Asn Ala Val Val Asn Glu Ser Lys Asn Thr Asn Asn Thr Glu Asn
                 85                  90                  95

Ala Val Val Asn Glu Asn Lys Asn Thr Asn Asn Thr Glu Asn Ala Val
            100                 105                 110

Val Asn Glu Asn Lys Asn Thr Asn Asn Thr Glu Asn Asp Asn Ser Gln
        115                 120                 125

Leu Lys Leu Thr Asn Asn Glu Gln Pro Ser Ala Ala Thr Gln Ala Asn
    130                 135                 140

Leu Lys Lys Leu Asn Pro Gln Ala Ala Lys Ala Val Gln Asn Ala Lys
145                 150                 155                 160

Ile Asp Ala Gly Ser Leu Thr Asp Asp Gln Ile Asn Glu Leu Asn Lys
                165                 170                 175

Ile Asn Phe Ser Lys Ser Ala Gly Lys Gly Ala Lys Leu Thr Phe Lys
            180                 185                 190

Asp Leu Glu Gly Ile Gly Asn Ala Ile Val Lys Gln Asp Pro Gln Tyr
        195                 200                 205

Ala Ile Pro Tyr Ser Asn Ala Lys Glu Ile Lys Asn Met Pro Ala Thr
    210                 215                 220

Tyr Thr Val Asp Ala Gln Thr Gly Lys Met Ala His Leu Asp Val Trp
225                 230                 235                 240
```

```
Asp Ser Trp Pro Val Gln Asp Pro Val Thr Gly Tyr Val Ser Asn Tyr
            245                 250                 255
Met Gly Tyr Gln Leu Val Ile Ala Met Met Gly Ile Pro Asn Ser Pro
            260                 265                 270
Thr Gly Asp Asn His Ile Tyr Leu Leu Tyr Asn Lys Tyr Gly Asp Asn
            275                 280                 285
Asp Phe Ser His Trp Arg Asn Ala Gly Ser Ile Phe Gly Thr Lys Glu
    290                 295                 300
Thr Asn Val Phe Gln Glu Trp Ser Gly Ser Ala Ile Val Asn Asp Asp
305                 310                 315                 320
Gly Thr Ile Gln Leu Phe Phe Thr Ser Asn Asp Thr Ser Asp Tyr Lys
                325                 330                 335
Leu Asn Asp Gln Arg Leu Ala Thr Ala Thr Leu Asn Leu Asn Val Asp
                340                 345                 350
Asp Asn Gly Val Ser Ile Lys Ser Val Asp Asn Tyr Gln Val Leu Phe
            355                 360                 365
Glu Gly Asp Gly Phe His Tyr Gln Thr Tyr Glu Gln Phe Ala Asn Gly
    370                 375                 380
Lys Asp Arg Glu Asn Asp Asp Tyr Cys Leu Arg Asp Pro His Val Val
385                 390                 395                 400
Gln Leu Glu Asn Gly Asp Arg Tyr Leu Val Phe Glu Ala Asn Thr Gly
                405                 410                 415
Thr Glu Asp Tyr Gln Ser Asp Asp Gln Ile Tyr Asn Trp Ala Asn Tyr
            420                 425                 430
Gly Gly Asp Asp Ala Phe Asn Ile Lys Ser Ser Phe Lys Leu Leu Asn
            435                 440                 445
Asn Lys Lys Asp Arg Glu Leu Ala Gly Leu Ala Asn Gly Ala Leu Gly
    450                 455                 460
Ile Leu Lys Leu Thr Asn Asn Gln Ser Lys Pro Lys Val Glu Glu Val
465                 470                 475                 480
Tyr Ser Pro Leu Val Ser Thr Leu Met Ala Cys Asp Glu Val Xaa Xaa
                485                 490                 495
Lys Leu Gly Asp Lys Tyr Tyr Leu Phe Ser Val Thr Arg Val Ser Arg
            500                 505                 510
Gly Ser Asp Arg Glu Leu Thr Ala Lys Asp Asn Thr Ile Val Gly Asp
            515                 520                 525
Asn Val Ala Met Ile Gly Tyr Val Ser Asp Ser Leu Met Gly Lys Tyr
            530                 535                 540
Lys Pro Leu Asn Asn Ser Gly Val Val Leu Thr Ala Ser Val Pro Ala
545                 550                 555                 560
Asn Trp Arg Thr Ala Thr Tyr Ser Tyr Tyr Ala Val Pro Val Ala Gly
                565                 570                 575
His Pro Asp Gln Val Leu Ile Thr Ser Tyr Met Ser Asn Lys Asp Phe
                580                 585                 590
Ala Ser Gly Glu Gly Asn Tyr Ala Thr Trp Ala Pro Ser Phe Leu Val
            595                 600                 605
Gln Ile Asn Pro Asp Asp Thr Thr Val Leu Ala Arg Ala Thr Asn
    610                 615                 620
Gln Gly Asp Trp Val Trp Asp Asp Ser Arg Asn Asp Asn Met Leu
625                 630                 635                 640
Gly Val Leu Lys Glu Gly Ala Ala Asn Ser Ala Ala Leu Pro Gly Glu
                645                 650                 655
Trp Gly Lys Pro Val Asp Trp Ser Leu Ile Asn Arg Ser Pro Gly Leu
```

```
                    660                 665                 670
Gly Leu Lys Pro His Gln Pro Val Gln Pro Lys Ile Asp Gln Pro Asp
            675                 680                 685

Gln Gln Pro Ser Gly Gln Asn Thr Lys Asn Val Thr Pro Gly Asn Gly
            690                 695                 700

Asp Lys Pro Ala Gly Lys Ala Thr Pro Asp Asn Thr Asn Ile Asp Pro
705                 710                 715                 720

Ser Ala Gln Pro Ser Gly Gln Asn Thr Asn Ile Asp Pro Ser Ala Gln
                725                 730                 735

Xaa Ser Gly Gln Asn Thr Lys Asn Val Thr Pro Gly Asn Glu Lys Gln
            740                 745                 750

Gly Lys Asn Thr Asp Ala Lys Gln Leu Pro Gln Thr Gly Asn Lys Ser
            755                 760                 765

Gly Leu Ala Gly Leu Tyr Ala Gly Ser Leu Leu Ala Leu Phe Gly Leu
            770                 775                 780

Ala Ala Ile Glu Lys Arg His Ala
785                 790

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 12
ctgataataa tggaaatgta tcac                                            24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
catgatcata agtttggtag taatag                                          26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 14
gtgatacatt tccattatta tcag                                            24

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
ctattactac caaacttatg atcatg                                          26

<210> SEQ ID NO 16
<211> LENGTH: 38
<212> TYPE: DNA
<213> ORGANISM: Artificial Sequence
```

```
<220> FEATURE:
<223> OTHER INFORMATION: Description of Artificial Sequence: Primer

<400> SEQUENCE: 16
ccatggccat ggtagaacgc aaggaacata aaaaaatg                            38

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 17
agatctagat ctgttaaatc gacgtttgtt aatttctg                            38

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (15)
<223> OTHER INFORMATION: a, c, t, g, other or unknown

<400> SEQUENCE: 18
gaygtntggg aywsntgggc c                                              21

<210> SEQ ID NO 19
<211> LENGTH: 23
<212> TYPE: DNA
<213> ORGANISM: Artificial Sequence
<220> FEATURE:
<221> NAME/KEY: modified_base
<222> LOCATION: (3)
<223> OTHER INFORMATION: a, c, t, g, other or unknown
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown
<220> FEATURE:
<221> NAME/KEY: modified_base
<222> LOCATION: (12)
<223> OTHER INFORMATION: a, c, t, g, other or unknown
<220> FEATURE:
<223> OTHER INFORMATION: Description of Artificial Sequence: Primer

<400> SEQUENCE: 19
gtngcnswnc cnswccayts ytg                                            23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20
gaatgtaggt ccaatttttg gc                                             22
```

```
<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
cctgtccgaa catcttgaac tg                                              22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: a, c, t, g, other or unknown
<220> FEATURE:
<221> NAME/KEY: modified_base
<222> LOCATION: (9)
<223> OTHER INFORMATION: a, c, t, g, other or unknown
<220> FEATURE:
<221> NAME/KEY: modified_base
<222> LOCATION: (12)
<223> OTHER INFORMATION: a, c, t, g, other or unknown
<220> FEATURE:
<221> NAME/KEY: modified_base
<222> LOCATION: (18)
<223> OTHER INFORMATION: a, c, t, g, other or unknown
<220> FEATURE:
<221> NAME/KEY: modified_base
<222> LOCATION: (21)
<223> OTHER INFORMATION: a, c, t, g, other or unknown

<400> SEQUENCE: 22
arraanswng gngcvmangt nsw                                             23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (9)
<223> OTHER INFORMATION: a, c, t, g, other or unknown
<220> FEATURE:
<221> NAME/KEY: modified_base
<222> LOCATION: (11)
<223> OTHER INFORMATION: a, c, t, g, other or unknown
<220> FEATURE:
<221> NAME/KEY: modified_base
<222> LOCATION: (15)
<223> OTHER INFORMATION: a, c, t, g, other or unknown
<220> FEATURE:
<221> NAME/KEY: modified_base
<222> LOCATION: (21)
<223> OTHER INFORMATION: a, c, t, g, other or unknown

<400> SEQUENCE: 23
tayaayggng tngcngargt naa                                             23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Primer
```

<400> SEQUENCE: 24
ccgaccatct tgtttgatta ac					22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
aaytataayg gygttgcryg aagt					24

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (9)
<223> OTHER INFORMATION: a, c, t, g, other or unknown

<400> SEQUENCE: 26
taccgnwsnc tacttcaact t					21

<210> SEQ ID NO 27
<211> LENGTH: 17
<212> TYPE: PRT
<213> ORGANISM: Lactobacillus reuteri

<400> SEQUENCE: 27

Tyr Asn Gly Val Ala Glu Val Lys Lys Arg Gly Tyr Phe Tyr Ala Arg
 1               5                  10                  15

Thr

<210> SEQ ID NO 28
<211> LENGTH: 17
<212> TYPE: PRT
<213> ORGANISM: Lactobacillus reuteri

<400> SEQUENCE: 28

Tyr Asn Gly Val Ala Glu Val Asn Thr Glu Arg Gln Ala Asn Gly Gly
 1               5                  10                  15

Ile

<210> SEQ ID NO 29
<211> LENGTH: 14
<212> TYPE: PRT
<213> ORGANISM: Bacillus amyloliquefaciens

<400> SEQUENCE: 29

Gly Leu Asp Val Trp Asp Ser Trp Pro Leu Gln Asn Ala Asp
 1               5                  10

<210> SEQ ID NO 30
<211> LENGTH: 14
<212> TYPE: PRT
<213> ORGANISM: Bacillus subtilis

<400> SEQUENCE: 30

Gly Leu Asp Val Trp Asp Ser Trp Pro Leu Gln Asn Ala Asp

-continued

<210> SEQ ID NO 31
<211> LENGTH: 14
<212> TYPE: PRT
<213> ORGANISM: Streptococcus mutans

<400> SEQUENCE: 31

Asp Leu Asp Val Trp Asp Ser Trp Pro Val Gln Asp Ala Lys
 1               5                  10

<210> SEQ ID NO 32
<211> LENGTH: 14
<212> TYPE: PRT
<213> ORGANISM: Streptococcus salivarius

<400> SEQUENCE: 32

Glu Ile Asp Val Trp Asp Ser Trp Pro Val Gln Asp Ala Lys
 1               5                  10

<210> SEQ ID NO 33
<211> LENGTH: 16
<212> TYPE: PRT
<213> ORGANISM: Bacillus amyloliquefaciens

<400> SEQUENCE: 33

Gln Thr Gln Glu Trp Ser Gly Ser Ala Thr Phe Thr Ser Asp Gly Lys
 1               5                  10                  15

<210> SEQ ID NO 34
<211> LENGTH: 16
<212> TYPE: PRT
<213> ORGANISM: Bacillus subtilis

<400> SEQUENCE: 34

Gln Thr Gln Glu Trp Ser Gly Ser Ala Thr Phe Thr Ser Asp Gly Lys
 1               5                  10                  15

<210> SEQ ID NO 35
<211> LENGTH: 16
<212> TYPE: PRT
<213> ORGANISM: Streptococcus mutans

<400> SEQUENCE: 35

Leu Thr Gln Glu Trp Ser Gly Ser Ala Thr Val Asn Glu Asp Gly Ser
 1               5                  10                  15

<210> SEQ ID NO 36
<211> LENGTH: 16
<212> TYPE: PRT
<213> ORGANISM: Streptococcus salivarius

<400> SEQUENCE: 36

Asp Asp Gln Gln Trp Ser Gly Ser Ala Thr Val Asn Ser Asp Gly Ser
 1               5                  10                  15

<210> SEQ ID NO 37
<211> LENGTH: 11
<212> TYPE: PRT
<213> ORGANISM: Bacillus amyloliquefaciens

<400> SEQUENCE: 37

Lys Ala Thr Phe Gly Pro Ser Phe Leu Met Asn
 1               5                  10

```
<210> SEQ ID NO 38
<211> LENGTH: 11
<212> TYPE: PRT
<213> ORGANISM: Bacillus subtilis

<400> SEQUENCE: 38

Gln Ser Thr Phe Ala Pro Ser Phe Leu Leu Asn
 1               5                  10

<210> SEQ ID NO 39
<211> LENGTH: 11
<212> TYPE: PRT
<213> ORGANISM: Streptococcus mutans

<400> SEQUENCE: 39

Asn Ser Thr Trp Ala Pro Ser Phe Leu Ile Gln
 1               5                  10

<210> SEQ ID NO 40
<211> LENGTH: 11
<212> TYPE: PRT
<213> ORGANISM: Streptococcus salivarius

<400> SEQUENCE: 40

Lys Ser Thr Trp Ala Pro Ser Phe Leu Ile Lys
 1               5                  10
```